United States Patent
Micheau et al.

(10) Patent No.: US 12,083,271 B2
(45) Date of Patent: Sep. 10, 2024

(54) LIQUID VENTILATOR AND METHOD TO INDUCE TIDAL LIQUID VENTILATION AND/OR HYPOTHERMIA

(71) Applicants: SOCPRA SCIENCES ET GENIE S.E.C., Sherbrooke (CA); ECOLE NATIONALE VETERINAIRE D'ALFORT, Maisons-Alfort (FR); INSTITUT NATIONAL DE LA SANTÉ ET DE LA RECHERCHE MÉDICALE, Paris (FR); UNIVERSITE PARIS EST CRETEIL VAL DE MARNE, Créteil (FR)

(72) Inventors: Philippe Micheau, Sherbrooke (CA); Renaud Tissier, Paris (FR); Matthias Kohlhauer, Saint-Maurice (FR); Julien Mousseau, Candiac (CA); Mathieu Nadeau, Compton (CA); Jonathan Vandamme, North Vancouver (CA)

(73) Assignees: SOCPRA SCIENCES ET GENIES S.E.C., Sherbrooke (CA); ECOLE NATIONALE VETERINAIRE D'ALFORT, Maisons-Alfort (FR); INSTITUT NATIONAL DE LA SANTÉ ET DE LA RECHERCHE MÉDICALE, Paris (FR); UNIVERSITE PARIS EST CRETEIL VAL DE MARNE, Créteil (FR)

(*) Notice: Subject to any disclaimer, the term of this patent is extended or adjusted under 35 U.S.C. 154(b) by 772 days.

(21) Appl. No.: 17/048,263

(22) PCT Filed: Apr. 12, 2019

(86) PCT No.: PCT/CA2019/050450
§ 371 (c)(1),
(2) Date: Oct. 16, 2020

(87) PCT Pub. No.: WO2019/200459
PCT Pub. Date: Oct. 24, 2019

(65) Prior Publication Data
US 2021/0077759 A1      Mar. 18, 2021

(30) Foreign Application Priority Data

Apr. 17, 2018  (EP) ..................................... 18020155
Apr. 17, 2018  (EP) ..................................... 18020156

(51) Int. Cl.
*A61M 16/00*       (2006.01)
*A61F 7/00*         (2006.01)
(Continued)

(52) U.S. Cl.
CPC ....... *A61M 16/0054* (2013.01); *A61F 7/0085* (2013.01); *A61F 7/12* (2013.01);
(Continued)

(58) Field of Classification Search
CPC ...... A61M 16/00; A61M 16/10; A61M 16/14; A61M 16/20; A61M 16/0054;
(Continued)

(56) References Cited

U.S. PATENT DOCUMENTS

| | | | |
|---|---|---|---|
| 2006/0278224 A1* | 12/2006 | Shaffer | A61M 16/0054 128/200.14 |
| 2012/0226337 A1 | 9/2012 | Tissier et al. | |
| 2016/0271348 A1 | 9/2016 | Nadeau et al. | |

FOREIGN PATENT DOCUMENTS

| | | | |
|---|---|---|---|
| CA | 2451261 A1 | 5/2004 | |
| WO | WO-9219300 A1 * | 11/1992 | ........ A61M 16/0054 |

(Continued)

OTHER PUBLICATIONS

Robert et al., "A Regulator for Pressure-Controlled Total-Liquid Ventilation", Institute of Electrical and Electronics Engineers Transactions on Biomedical Engineering, vol. 57, No. 9, Sep. 2010, pp. 2267-2276.
(Continued)

*Primary Examiner* — Elliot S Ruddie
*Assistant Examiner* — Maap Ahmed Ellabib
(74) *Attorney, Agent, or Firm* — Maier & Maier, PLLC

(57) ABSTRACT

Liquid ventilator and methods integrating the concept of total liquid ventilation (TLV) using liquid volumes below functional residual capacity (FRC) of mammal's lungs are (Continued)

disclosed. Beyond the automatization of the whole process, the technology has been up-scaled to confirm that TLV at residual volumes below FRC can provide a safe procedure while enabling the full potential of TLV in a mammal such as humans or adult-sized animals. Such tidal liquid ventilation strongly differs from the previously known TLV approach, opening promising perspectives for a safer clinical translation. Also disclosed are apparatus and method for safe and fast induction of hypothermia during liquid ventilation of a mammal.

19 Claims, 20 Drawing Sheets

(51) Int. Cl.
*A61F 7/12* (2006.01)
*A61M 16/08* (2006.01)
*A61M 16/10* (2006.01)
*A61M 16/20* (2006.01)

(52) U.S. Cl.
CPC ...... *A61M 16/0003* (2014.02); *A61M 16/024* (2017.08); *A61M 16/1005* (2014.02); *A61M 16/1075* (2013.01); *A61F 2007/0064* (2013.01); *A61F 2007/0086* (2013.01); *A61F 2007/126* (2013.01); *A61M 2016/0027* (2013.01); *A61M 2016/0036* (2013.01); *A61M 16/0051* (2013.01); *A61M 16/0833* (2014.02); *A61M 16/208* (2013.01); *A61M 2202/02* (2013.01); *A61M 2202/0476* (2013.01); *A61M 2205/3368* (2013.01); *A61M 2205/3606* (2013.01); *A61M 2205/366* (2013.01); *A61M 2230/46* (2013.01)

(58) Field of Classification Search
CPC ........... B63C 2011/2263; B63C 11/184; B63C 11/12; B63C 11/18
See application file for complete search history.

(56) References Cited

FOREIGN PATENT DOCUMENTS

| WO | WO-9408652 A1 * | 4/1994 | ........ A61M 16/0054 |
|----|-----------------|--------|------------------------|
| WO | WO-03047603 A2 * | 6/2003 | ............. A61K 33/00 |
| WO | 2012062266 A1 | 5/2012 | |

OTHER PUBLICATIONS

Micheau et al., "A Liquid Ventilator Prototype for Total Liquid Ventilation Preclinical Studies", Progress in Molecular and Environmental Bioengineering—From Analysis and Modeling to Technology Applications, Aug. 2011, pp. 1-23.

International Search Report issued on Jun. 18, 2019 in corresponding International application No. PCT/CA2019/050450; 6 pages.

Robert et al., "A supervisor for volume-controlled tidal liquid ventilator using independent piston pumps" Biomedical Signal Processing and Control 2, Sep. 2007 (Sep. 2007), pp. 267-274., 9 pgs.

Nadeau et al., "Core Body Temperature Control by Total Liquid Ventilation Using a Virtual Lung Temperature Sensor". IEEE Transactions on Biomedical Engineering, Dec. 2014 (Dec. 2014), vol. 61(12), pp. 2859-2868., 10 pgs.

Nadeau et al., "Patient-specific optimal cooling power command for hypothermia induction by liquid ventilation" Control Engineering Practice, Jun. 2018, pp. 109-117., 9 pgs.

* cited by examiner (A)

(B)

LIQUID VENTILATOR AND METHOD TO INDUCE TIDAL LIQUID VENTILATION AND/OR HYPOTHERMIA

CROSS-REFERENCE TO RELATED INVENTIONS

This is a National Stage Application of International Application No. PCT/CA/2019/050450, filed Apr. 12, 2019, which claims priority based upon the prior patent applications: No. EP18020155.0 entitled in English "Method and device for determining and preventing an expiratory collapse", and No. EP18020156.8 entitled "Method and device for determining and preventing a low temperature", both filed at the European Patent Office on Apr. 17, 2018, the content of these applications being herein incorporated by reference in their entirety.

FIELD

The present invention relates to the field of artificial ventilators and, more particularly, to airway pressure and lung temperature.

BACKGROUND

Artificial mechanical ventilation concepts include mechanical ventilators, high frequency ventilators, and could be extended to other devices such as extracorporeal membrane oxygenation (ECMO) devices. Total liquid ventilation (TLV) is a radical departure from these concepts. Total liquid ventilation (TLV) of the lungs could provide radically new benefits in critically ill patients requiring lung lavage or ultra-fast cooling after cardiac arrest. It consists in an initial filling of the lungs with liquid, for example perfluorocarbon (PFC), and subsequent tidal ventilation using a dedicated liquid ventilator providing a cyclic respiratory volume renewal.

Unfortunately, the deployment and use of the TLV technology in a clinical setting has been limited. The present invention aims at providing at least partial solutions to problems that are seen as limiting such deployment and use.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A first aspect of the present invention is directed to a ventilator for liquid ventilation of a mammal comprising: ventilator for liquid ventilation of a mammal comprising:
  a respiratory circuit defining an inspiratory circuit and an expiratory circuit, and comprising:
    an oxygenator for oxygenating a breathable liquid; and
    a pumping assembly operatively connected to the oxygenator for pumping the breathable liquid in and out of the mammal's lungs through the respiratory circuit;
  a pressure sensor operatively connected to the respiratory circuit and configured to measure a pressure of a respiratory flow of the breathable liquid; and
  a control unit operatively connected to the pressure sensor and the pumping assembly for controllably exchanging the breathable liquid between the oxygenator and the mammal's lungs while controlling the expiratory flow of the breathable liquid pumped out of the lungs;
  wherein the control unit comprises a processor for:
    effecting in real-time a pressure P calculated from the measured pressure; and when the pressure P reaches a negative threshold indicating a collapse of the mammal's trachea, reducing in real-time the expiratory flow of the breathable liquid according to a factor R while pumping the breathable liquid out of the lungs during a given expiratory period of time in order to maintain a targeted end-expiratory breathable liquid volume, or EEBLV, in the mammal's lungs.

According to a preferred embodiment, the targeted EEBLV is between 10 and 20 ml/Kg for a respiratory frequency of between 2 and 8 rpm and a tidal volume of breathable liquid of between 4 to 10 mL/Kg.

According to a preferred embodiment, the negative threshold of the pressure P is equal or inferior to about −50 cmPhO and the given expiratory period of time during which the pumping assembly pumps the breathable liquid out of the lungs allows removing at least 80% of the targeted tidal expiratory volume of the breathable liquid.

According to a preferred embodiment, the ventilator further comprises a reservoir located at a level below the mammal and fluidly connected to the pumping assembly, wherein the control unit is further configured to open in real-time the respiratory circuit when the pressure P reaches a critical pressure inferior to about −130 cmfhO or superior to about +130 cmfhO in order to generate a low negative pressure P (such as a negative pressure P close to 0 cmPhO) to drain the breathable liquid from the lungs by gravity towards the reservoir.

According to a preferred embodiment, the ventilator further comprises an alarm unit operatively connected to the control unit for triggering an alarm when the critical pressure is reached.

According to a preferred embodiment, the pressure of the respiratory flow is measured at the mouth of the mammal.

According to a preferred embodiment, the pumping assembly comprises:
  a Y connector comprising a junction for connecting the pumping assembly to a proximal end of an endotracheal tube having a distal end insertable in the mammal's trachea;
  an expiratory pump fluidly connected to the junction of the Y connector and upstream to the oxygenator;
  an inspiratory pump fluidly connected to the junction of the Y connector and downstream to the oxygenator; and
  a plurality of valves, each valve being independently controlled by the control unit for driving the breathable liquid going through the expiratory and inspiratory pumps and guiding the breathable liquid to the lungs.

According to a preferred embodiment, the ventilator further comprises a cooling unit fluidly connected to the oxygenator, the cooling unit producing a cooling fluid at a cooling temperature for cooling and/or maintaining an inspiratory temperature of the breathable liquid going through the oxygenator before being driven to the mammal's lungs.

According to a preferred embodiment, the cooling unit is in fluid communication with the oxygenator for receiving the cooling fluid therefrom, the cooling fluid being then cooled while going through the cooling unit; the ventilator further comprising a pump in fluid communication with the cooling unit and the oxygenator for pumping back the cooling fluid from the cooling unit to the oxygenator where the cooling fluid thermally exchanges with the breathable liquid of the ventilator circulating in the oxygenator for cooling the breathable liquid before the re-instillation of the breathable liquid into the mammal's lung.

According to a preferred embodiment, the ventilator further comprises a temperature sensor for measuring an expiratory temperature of the breathable liquid pumped out of the mammal's lungs, the temperature sensor being operatively connected to the control unit, the control unit being further configured to adjust the cooling temperature of the cooling fluid by controlling the pump and therefore controlling a flow of cooling fluid going through the cooling unit and the oxygenator in order to adjust the temperature of the breathable liquid in function of the measured expiratory temperature. Preferably, controlling the pump consists in turning on the pump during a first pre-set period of time and turning off the pump during a first pre-set period of time to control the flow of cooling liquid.

A second aspect of the present invention is directed to the use of a targeted end-expiratory breathable liquid volume, or EEBLV, of a breathable liquid inferior to a functional residual capacity, or FRC, of the lungs of a mammal for preventing deleterious effects on the mammal's lungs during a liquid ventilation of said mammal. Preferably, the EEBLV is between 10 and 20 ml/Kg for a respiratory frequency of between 2 and 8 rpm and a tidal volume of the breathable liquid of 4 to 10 mL/Kg.

A third aspect of the present invention is directed to a method for liquid ventilation of a mammal comprising the steps of:
  a) pumping a breathable liquid in and out of the lungs of the mammal according to a respiratory flow while measuring a pressure of the respiratory flow of the breathable liquid;
  b) effecting in real-time a pressure P calculated from the measured expiratory pressure; and
  c) when the pressure P reaches a negative threshold indicating a collapse of the mammars trachea, reducing in real-time the expiratory flow of the breathable liquid according to a factor R while pumping the breathable liquid out of the lungs during a given expiratory period of time in order to maintain a targeted end-expiratory breathable liquid volume, or EEBLV, in the mammal's lungs.

According to a preferred embodiment, the EEBLV in the method is between 10 and 20 ml/Kg for a respiratory frequency of between 2 and 8 rpm and a tidal volume of breathable liquid of between 4 and 10 mL/Kg.

According to a preferred embodiment, the negative threshold of the pressure P is equal or inferior to about −50 cmfhO, and wherein the given expiratory period of time during which the breathable liquid is pumped out of the lungs allows removing at least 80% of the volume of the breathable liquid.

According to a preferred embodiment, the method further comprises the step of evacuating the breathable liquid from the mammal's lungs when the pressure P is a critical value inferior to about −130 cmEhO or superior to about +130 cmEhO.

According to a preferred embodiment, the method further comprises the step of triggering an alarm when the critical value is reached.

According to a preferred embodiment, the method further comprises the step of cooling and/or maintaining a temperature of the breathable liquid while pumping the breathable liquid in and out of the lungs of the mammal. Preferably, the step of cooling and/or maintaining the temperature of the breathable liquid comprises: producing a cooling fluid, and thermally exchanging the cooling fluid with the breathable liquid for cooling the breathable liquid before re-instilling the breathable liquid into the mammal's lung.

According to a preferred embodiment, the method further comprises the steps of: measuring an expiratory temperature of the breathable liquid pumped out of the mammal's lungs; and adjusting a temperature of the cooling fluid in function of the measured expiratory temperature for adjusting the temperature of the breathable liquid pumped into the lungs.

According to a preferred embodiment, the step of adjusting the temperature of the cooling fluid consists in maintaining a flow of the cooling fluid during a first pre-set period of time, or stopping said flow during a second pre-set period of time, when the cooling fluid thermally exchanges with the breathable liquid.

A fourth aspect of the present invention is directed to an apparatus for safe induction of hypothermia during liquid ventilation of a mammal, the apparatus comprising:
  a cooling unit configured to produce a cooling fluid at a cooling temperature when the cooling fluid circulates through the cooling unit, the cooling unit being in fluid communication with an oxygenator of a liquid ventilator for receiving the cooling fluid therefrom; and
  a controllable pumping unit in fluid communication with the oxygenator and the cooling unit, the controllable pumping unit being configured to pump back the cooling fluid from the cooling unit to the oxygenator module where the cooling fluid thermally exchanges with a breathable liquid of the liquid ventilator circulating in the oxygenator module for controlling an inspiratory temperature of the breathable liquid oxygenated by the oxygenator before the re-instillation of the cooled oxygenated breathable liquid into the mammal's lung;
  wherein the liquid ventilator comprises a temperature sensor for measuring in real-time an expiratory temperature of the breathable liquid pumped out of the mammal's lungs, the temperature sensor being operatively connected to the controllable pumping unit to modify a flow of the cooling fluid and therefore to adjust the inspiratory temperature of the breathable liquid in function of the measured expiratory temperature.

According to a preferred embodiment, the control of the pumping unit consists in turning on the pumping unit during a first pre-set period of time and turning off the pumping unit during a second pre-set period of time to control the flow of cooling liquid going through the cooling unit and the oxygenator.

According to a preferred embodiment, the pumping unit is configured to pump the cooling fluid at a controlled mass flow rate in order to control a cooling power of the thermal exchange in the oxygenator.

According to a preferred embodiment, the pump is operatively connected to a processor module of the liquid ventilator configured to control the mass flow rate of the cooling fluid and as such to vary the temperature of the breathable liquid in the oxygenator.

According to a preferred embodiment, the cooling fluid may comprise water.

A fourth aspect of the present invention is directed to a method for induction of hypothermia in a mammal comprising the steps of:
  a) producing a cooling fluid at a cooling temperature with a cooling unit;
  b) controllably circulating the cooling fluid through an oxygenator of a liquid ventilator where the cooling fluid thermally exchanges with a breathable liquid of the ventilator for controlling an inspiratory temperature of the breathable liquid oxygenated by the oxygenator before re-instilling the breathable liquid into the mammal's lung;

c) measuring in real-time an expiratory temperature of the breathable liquid pumped out of the mammal's lungs; and d) adjusting in real-time the inspiratory temperature of the breathable liquid in function of the expiratory temperature measured in step c) by modifying a flow of the cooling fluid circulating through the cooling unit and the oxygenator.

According to a preferred embodiment, modifying the flow of the cooling fluid circulating through the cooling unit and the oxygenator consists in circulating the cooling fluid during a first pre-set period of time and stopping the circulation of the cooling liquid during a second pre-set period of time.

According to a preferred embodiment, the method further comprises the step of varying a mass flow rate of the cooling liquid circulating into the oxygenator for controlling a cooling power of the thermal exchange in the oxygenator.

According to a preferred embodiment, the method further comprises the step of varying the temperature of the breathable liquid circulating in the oxygenator by varying the mass flow rate of the cooling liquid circulating in the cooling unit.

According to a preferred embodiment, the cooling fluid comprises water.

For all aspect of the invention disclosed herein, the breathable liquid may preferably comprises perfluorocarbons, or PFC, and the mammal is preferably a human.

Other and further aspects and advantages of the present invention will be better understood upon the reading of the illustrative embodiments about to be described or will be indicated in the appended claims, and various advantages not referred to herein will occur to one skilled in the art upon employment of the invention in practice.

BRIEF DESCRIPTION OF THE DRAWINGS

Further features and exemplary advantages of the present invention will become apparent from the following detailed description, taken in conjunction with the appended drawings, in which.

DETAILED DESCRIPTION

Figure 1:
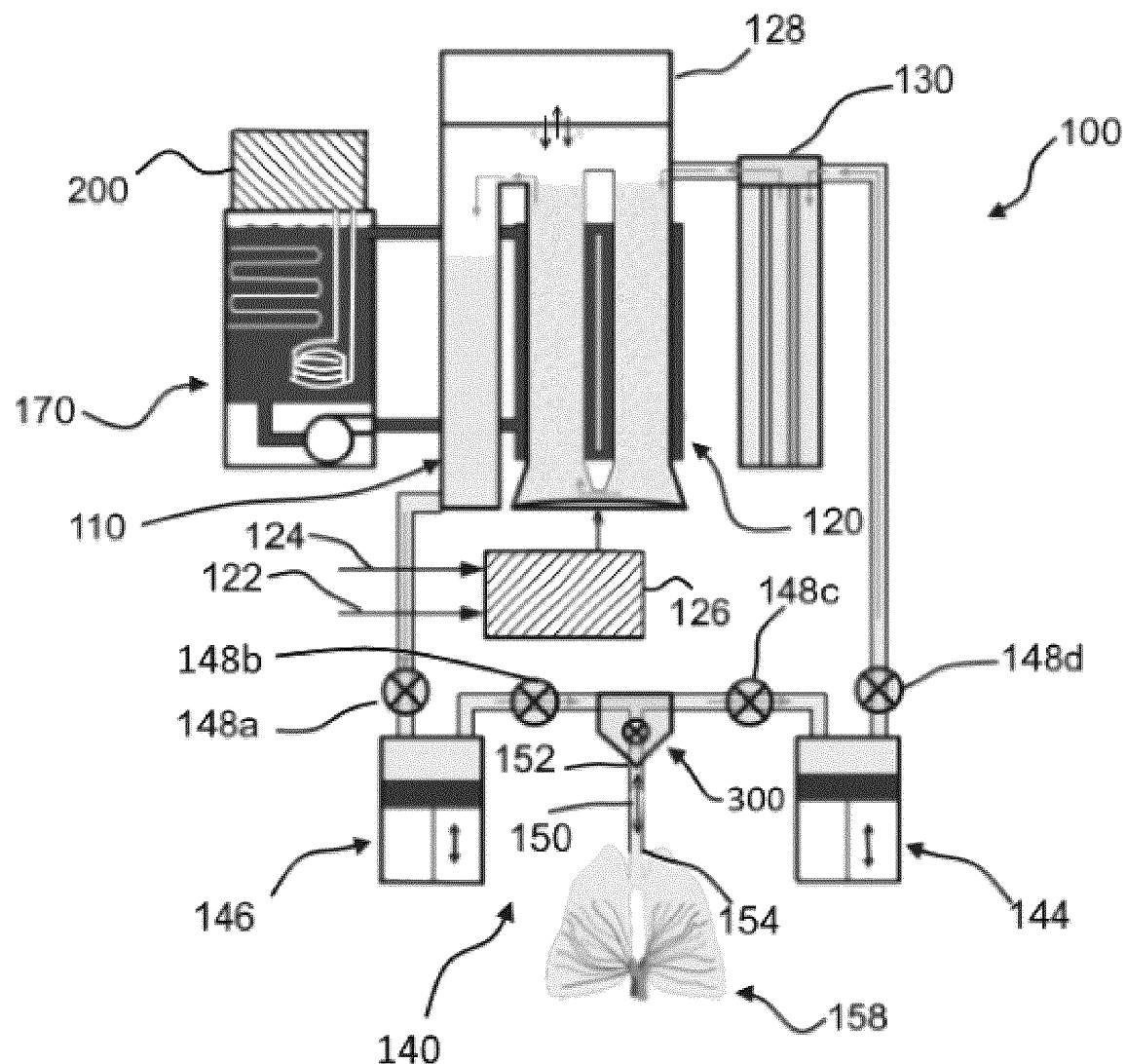
FIG. 1 is a schematic illustration of a liquid ventilator according to an embodiment of the present invention.

A novel ventilator, apparatus and methods will be described hereinafter. Although the invention is described in terms of specific illustrative embodiments, it is to be understood that the embodiments described herein are by way of example only and that the scope of the invention is not intended to be limited thereby.

The development of protective mechanical ventilation have been a major step forward for critically ill patients in intensive care units over the last decades. One of the next medical breakthroughs is the use of total liquid ventilation (TLV) of the lungs with residual volumes of perfluorocarbons, above which a tidal volume of liquid is added and removed at each respiratory cycle. Due to the high solubility of the PFC for gases, TLV can ensure normal gas exchanges and provides pulmonary benefits, as shown in animal models of respiratory diseases. When afforded with temperature-controlled PFC, it can also use the lungs as heat exchangers and afford ultra-fast cooling and potent experimental neuroprotection after resuscitated cardiac arrest. However, its clinical translation was limited by the lack of liquid ventilators able to adequately control PFC pulmonary flows during TLV and the absence of consensus regarding adequate respiratory parameters.

A new apparatus has been developed that can continuously regulate expiratory flow as well as PFC volumes and pressures, which was a great cornerstone for TLV translation. At this step, precise recommendations are still needed to provide an efficient procedure, regarding targeted PFC volumes, filling pressures and PFC target temperatures.

The importance of such recommendations is supported by previous clinical experiences with other techniques of liquid ventilation. The conventional gaseous ventilation of PFC-filled lungs, also known as partial liquid ventilation, was indeed associated with increased occurrence of volu- or barotrauma in patients presenting with acute-respiratory distress syndrome. Those results showed that we poorly understood the pulmonary response to liquid filling and still need precise guidelines for ideal lung pressures, residual and tidal volumes. TLV is radically different from PLV, as it allows a tidal liquid ventilation, but the evaluation of lung mechanics at different levels of lung filling and the delayed effects on lung recovery are also still lacking. It is now important to assess properly this phenomenon as TLV could allow opening unique perspectives in critical care patients.

A new, fully safe and protective approach for TLV that allows tidal ventilation of the lungs after incomplete lung filling with PFC is disclosed herein. Different strategies with various filling and tidal volumes have been tested to determine the procedure with the best tolerance through liquid redistribution into initially partly filled lungs rather than inflation of fully filled lungs. This showed that TLV could be much better tolerated when the lungs are filled below the expected volume of the functional residual capacity (FRC), despite incomplete initial degassing. The invention has been tested in piglets. Beyond being safe, this procedure could still be beneficial through its ultra-fast cooling properties.

The foregoing and other features will become more apparent upon reading of the following non-restrictive description of illustrative embodiments thereof, given by way of example only with reference to the accompanying drawings. Like numerals represent like features on the various drawings.

According to a preferred embodiment, the invention consists in integrating the concept of TLV using liquid volumes below FRC using a new liquid ventilator. Beyond the automatization of the whole process, the technology has been up-scald to confirm that TLV at residual volumes below FRC can provide a safe procedure while enabling the full potential of TLV in a mammal such as humans or adult-sized animals. Such tidal liquid ventilation strongly differs from the previously known TLV approach, opening promising perspectives for a safer clinical translation.

A liquid ventilator in accordance with preferred embodiment of the invention are illustrated on FIGS. 1 to 6. The ventilator (100) for liquid ventilation of a mammal comprises a liquid circuit forming a loop, and including first a reservoir (110) configured to contain a breathable liquid (BL), and an oxygenator (120) fluidly connected to the reservoir (110) for oxygenating the breathable liquid. As illustrated on FIG. 5, the reservoir (110) and the oxygenator (120) may alternatively form a unique assembly where the reservoir is integrated into the oxygenator. In another embodiment, there is no reservoir (not illustrated).

Figure 6A:
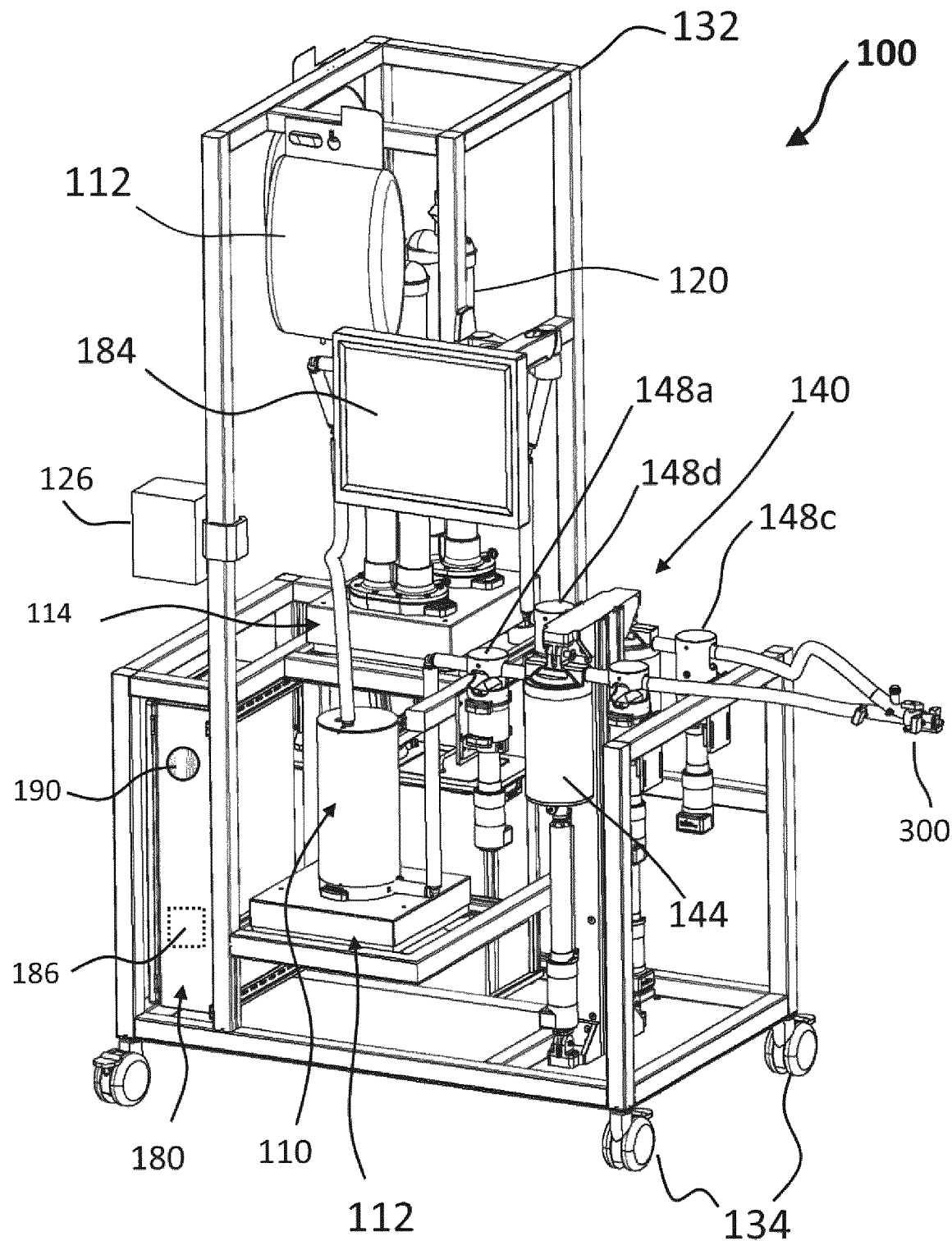
FIGS. 6A and 6B show a three-dimensional illustration of the ventilator according to an embodiment of the present invention.
Figure 6B:
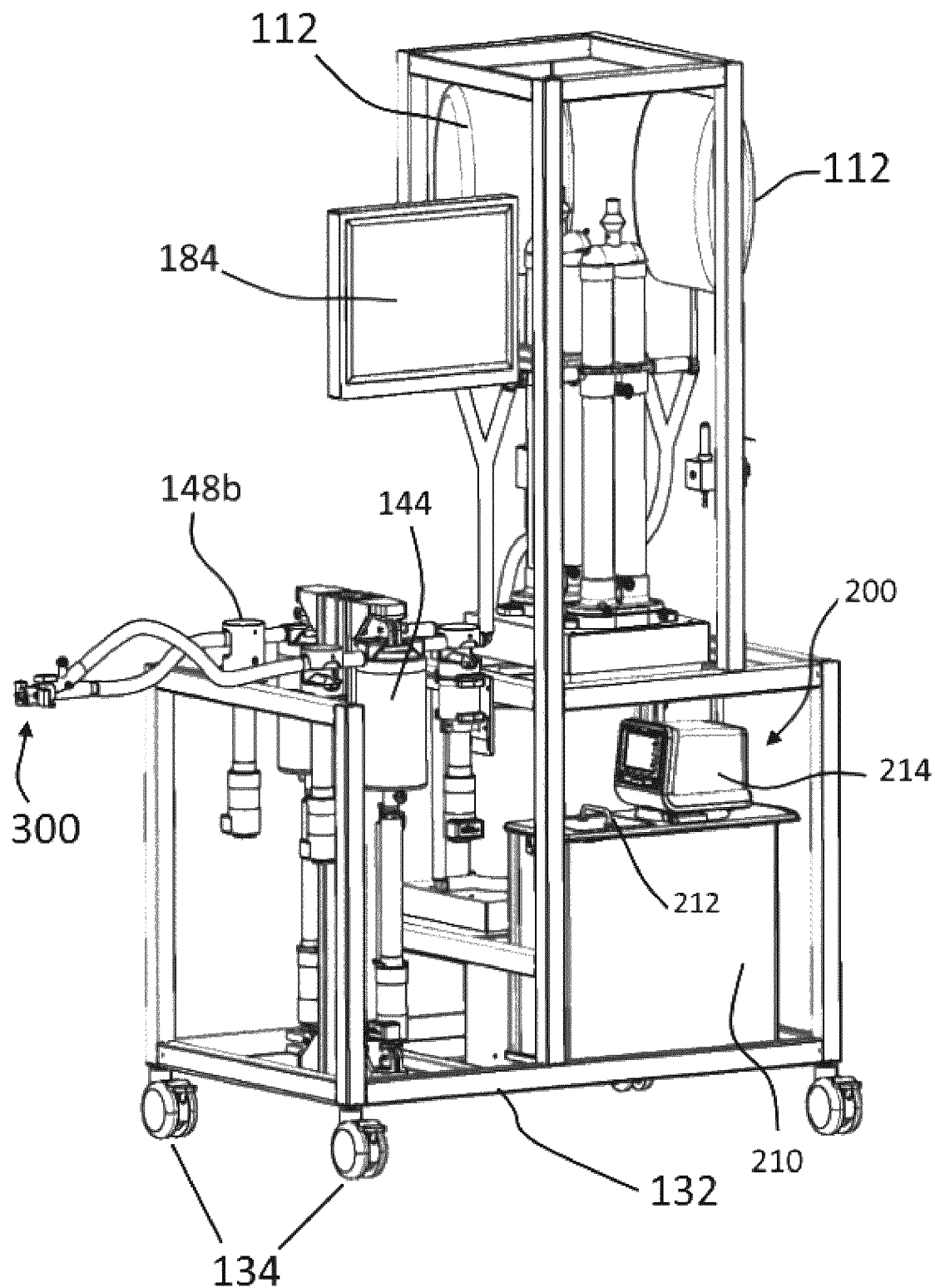

The ventilator (100) as shown on FIGS. 6A and 6B may have a pair of pockets suspended in a upper section of the ventilator for containing the BL that will be distributed into the ventilator at the beginning of the ventilation process. Also, the ventilator is supported by a frame (112) that can be moved thanks to a plurality of wheels (134). The ventilator may also have a first scale (114) located under the reservoir (110) and/or a second scale (114) located under the oxygenator (120). The scales are operatively connected to the control unit (180) in order to determine in real-time the amount of BL contained in the reservoir and/or the oxygenator and to calculate therefore the volume of BL in the mammal's lungs.

The oxygenator is configured to receive a mixture of air (122) and dioxygen—O2 gas (124) pre-mixed in a gas blender (126). The ventilator may also comprise a gas condenser (128) typically located above the reservoir, or adjacent a top section of the oxygenator, for condensing the breathable liquid (BL) and limits its loss. The ventilator (100) may optionally comprises a filtering unit (130) upstream the oxygenator for filtering the breathable liquid (BL) before entering the oxygenator. Reservoirs, oxygenators, gas blender, filters, tubing and condenser such as those known in the art of TLV technology can be used in connection with the present invention.

The ventilator (100) also comprises a pumping assembly (140) operatively connected to the reservoir (110) and the oxygenator (120) for pumping the breathable liquid (BL). As illustrated in FIGS. 1-4, the pumping assembly may comprise a Y connector (300) comprising a junction for connecting the pumps to a proximal end (152) of an endotracheal tube (150) having a distal end (154) insertable in the mammal's trachea (156). Preferably, the pumping assembly (140) comprises a first expiratory pump (144) fluidly connected to the Y connector (300) for pumping the breathable liquid out of the lungs (158) toward the filter (130) and then the oxygenator (120) before reaching the optional reservoir (110) where a reserve of oxygenated breathable liquid may be stored. The pump assembly (140) then also comprises an inspiratory pump (146) fluidly connected to the reservoir (110) for injecting the oxygenated breathable liquid pre-stored in the reservoir into the lungs through the Y connector (150) closing as such the loop circuit of the ventilator. The pumping assembly further comprises a plurality of valves (148), typically four valves (148*a*, 148*b*, 148*c*, 148*d*), which in connection with the two pumps (144, 146), the tubes and Y connector, allow driving the breathable liquid (BL) going through the expiratory and inspiratory pumps and guiding the breathable liquid to the lungs.

Figures 3, 4:
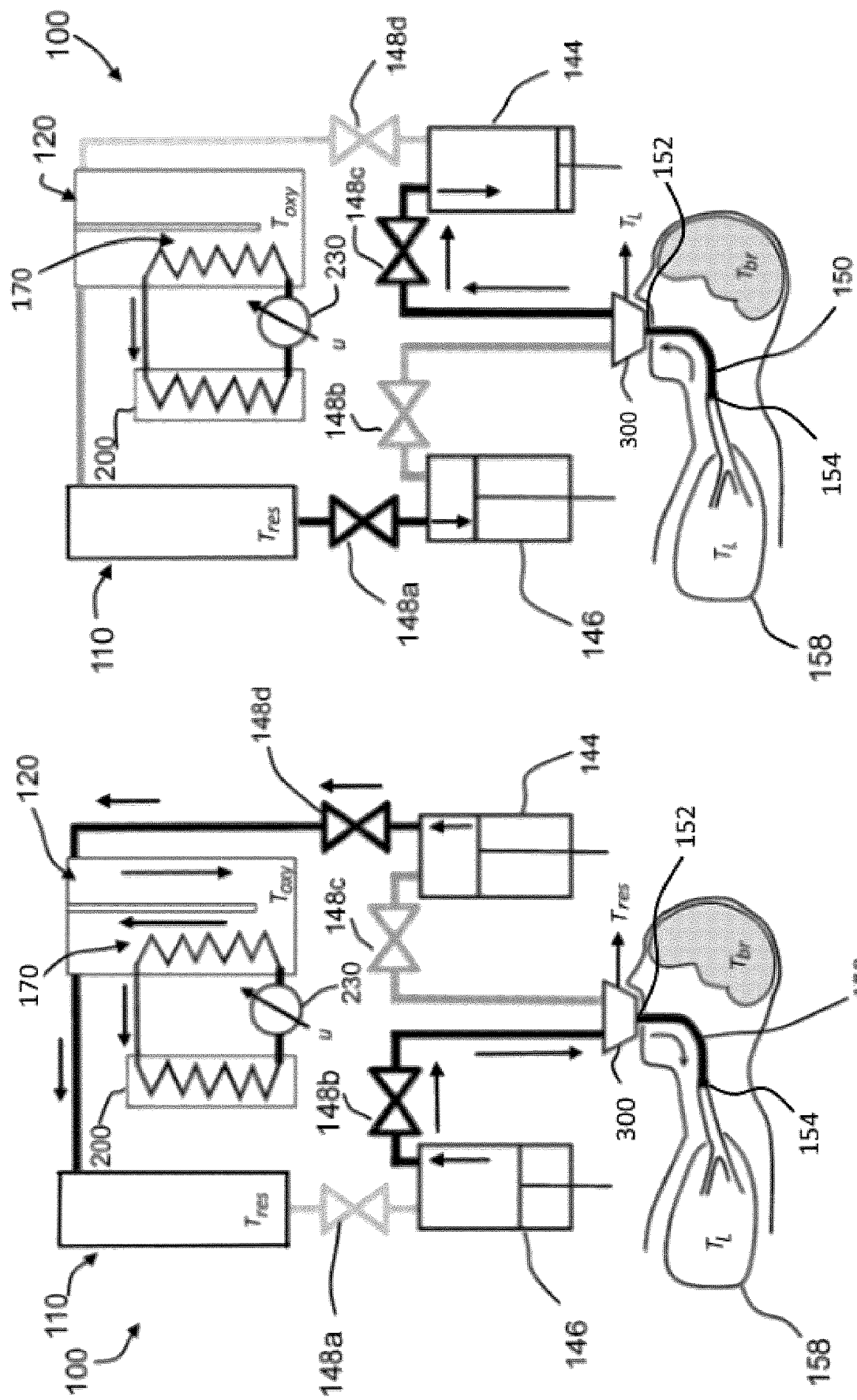
FIG. 3 is a schematic representation of the liquid ventilator according to an embodiment of the present invention connected to a patient function during inspiration phase.
FIG. 4 is a schematic representation of the liquid ventilator according to an embodiment of the present invention connected to a patient function expiration phase.
Figure 5:
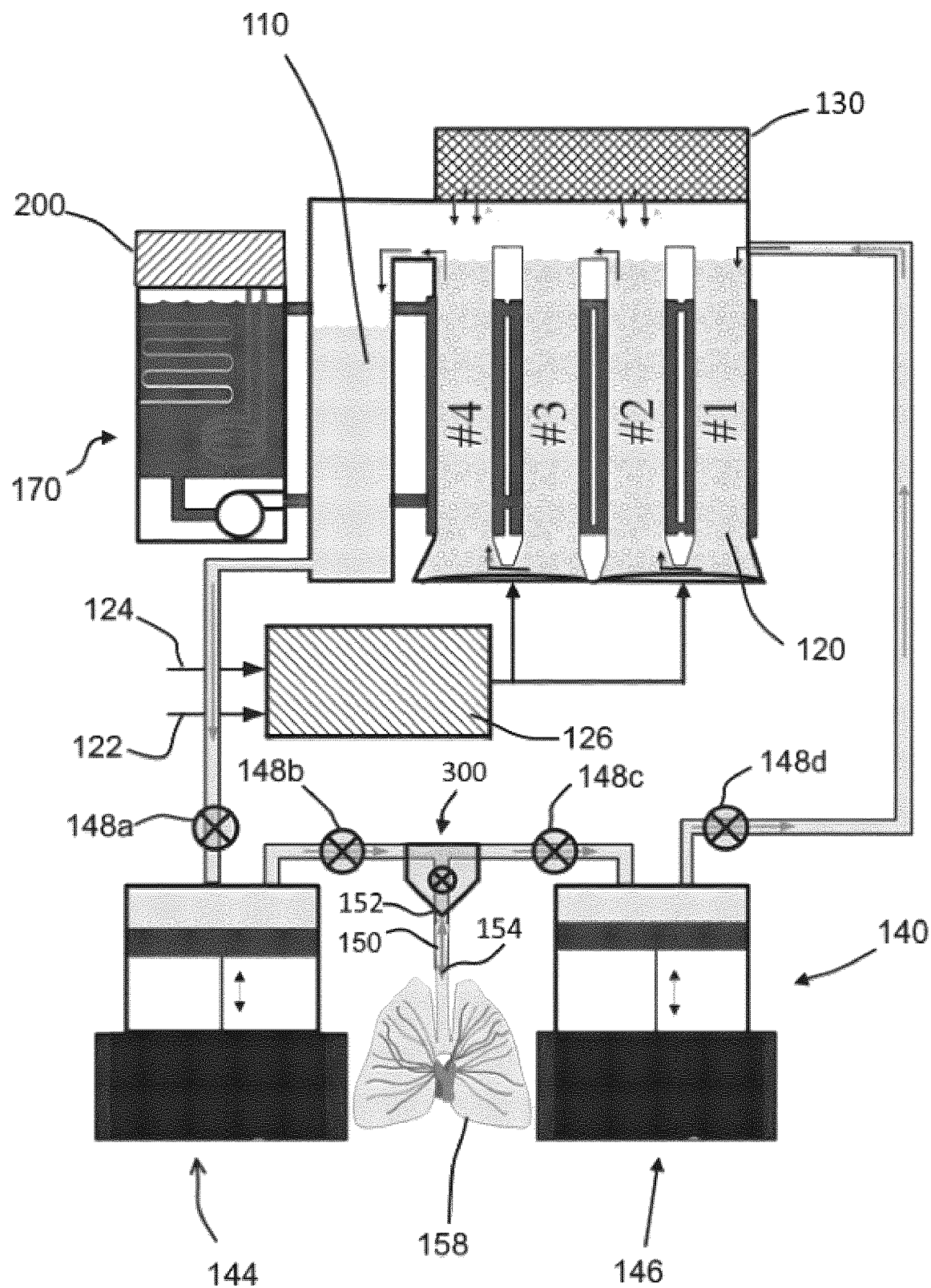
FIG. 5 is a schematic illustration of an up-scaled liquid ventilator according to another embodiment of the present invention.

The functions of a ventilator in accordance with a preferred embodiment of the invention are schematically illustrated on FIG. 4 during inspiration and FIG. 5 expiration, with:
 (158): lungs (VL: perfluorocarbon volume in the lung; TL: lung temperature);
 (144), expiratory pump;

(146): inspiratory pump;
(148a-d): pinch valves;
(120): oxygenator (Vresperfluorocarbon volume in the oxygenator, Tresperfluorocarbon temperature in the oxygenator);
(110): reservoir (Vresperfluorocarbon volume in the reservoir, Tresperfluorocarbon temperature in the reservoir);
(300): Y-connector; and
(170): Thermal exchanger.

The ventilator (100) is connected to the patient via the Y-connector (300). The four pinch valves (148a, 148b, 148c, 148d) are programmed to guide the liquid flow (BL) to the lungs (158). During the inspiration phase, the valves (148b) and (148d) are open and the valves (148a) and (148c) are closed. The inspiratory pump (146) inserts the respiratory PFC (BL) through the endotracheal tube (150) to the lungs (158). Hence the liquid arrives directly to the lung (158) from the reservoir (110) at the controlled temperature Tres. Simultaneously, the expiratory pump (144) returns a tidal volume of liquid (previously expired from the lung (158)) to the oxygenator (120). During the expiration phase (B), the valves (148b) and (148d) are closed, and the valves (148a) and (148c) are open. The expiratory pump (144) withdraws the liquid (e.g. PFC) through the endotracheal tube (150) from the lungs (158). Simultaneously, the inspiratory pump (146) is filled with a tidal volume of liquid (BL) pumped from the reservoir (110). The liquid temperature that directly arrives from the lung (158) is measured at the patient connector location (300). At the end of expiration, this temperature measurement at the Y-connector (300) can be used to calculate an indirect measurement of the lung temperature TL, as detailed and explained in international patent application no. WO 2014/205548 A1 (Nadeau et al), published on Dec. 31, 2014, the content of which is incorporated herein by reference.

The function of the oxygenator (120) is to oxygenate the liquid (BL) and to control its temperature. Dioxygen (O2) and carbon dioxide (CO2) concentrations in the PFOB is monitored and controlled by the gas mixer (See 126, FIG. 1). Water flowing within the double walls of the oxygenator (120) is used for cooling the liquid (e.g. PFC) inside the oxygenator before its re instillation into the lungs. A cooling fluid (CF), such as one comprising cold water, is pumped from a cooling system (200) to the oxygenator (120) at a controlled mass flow rate with a pump (210). Hence, the command u of the pump (210) allows controlling the cooling power (CP) of the thermal exchange in the oxygenator (120). When there is no inflow of CF in the oxygenator there is no cooling power in the latter, and u=0. When there is maximal inflow of CF in the oxygenator, the maximal cooling power is applied to the oxygenator.

The liquid ventilator is designed to initiate liquid ventilation with a breathable liquid (e.g. PFC) at a controlled hospital room temperature (e.g. about 20° C.) and with a global volume of liquid such that no heat extraction from the liquid (BL) is required during the first 2 min. There is no need for a cooling power control during the first instillation of liquid and the start of liquid ventilation. In terms of control problems, the input variable u of the pumping system is assumed to directly command the cooling power, u=−P (in W). The output variable is the lung temperature TL.

As used herein, the term "about" indicates that the average value may vary up to 10% above or below the stated value.

As illustrated on FIG. 1, the ventilator (100) also comprises a pressure sensor (160) operatively connected to the respiratory circuit and configured to measure a pressure of a respiratory flow of the breathable liquid. For instance, the pressure sensor can measure the pressure at the mouth of the patient. For instance, the pressure sensor can be located inside the Y-connector (300) together with a temperature sensor.

Figure 17:
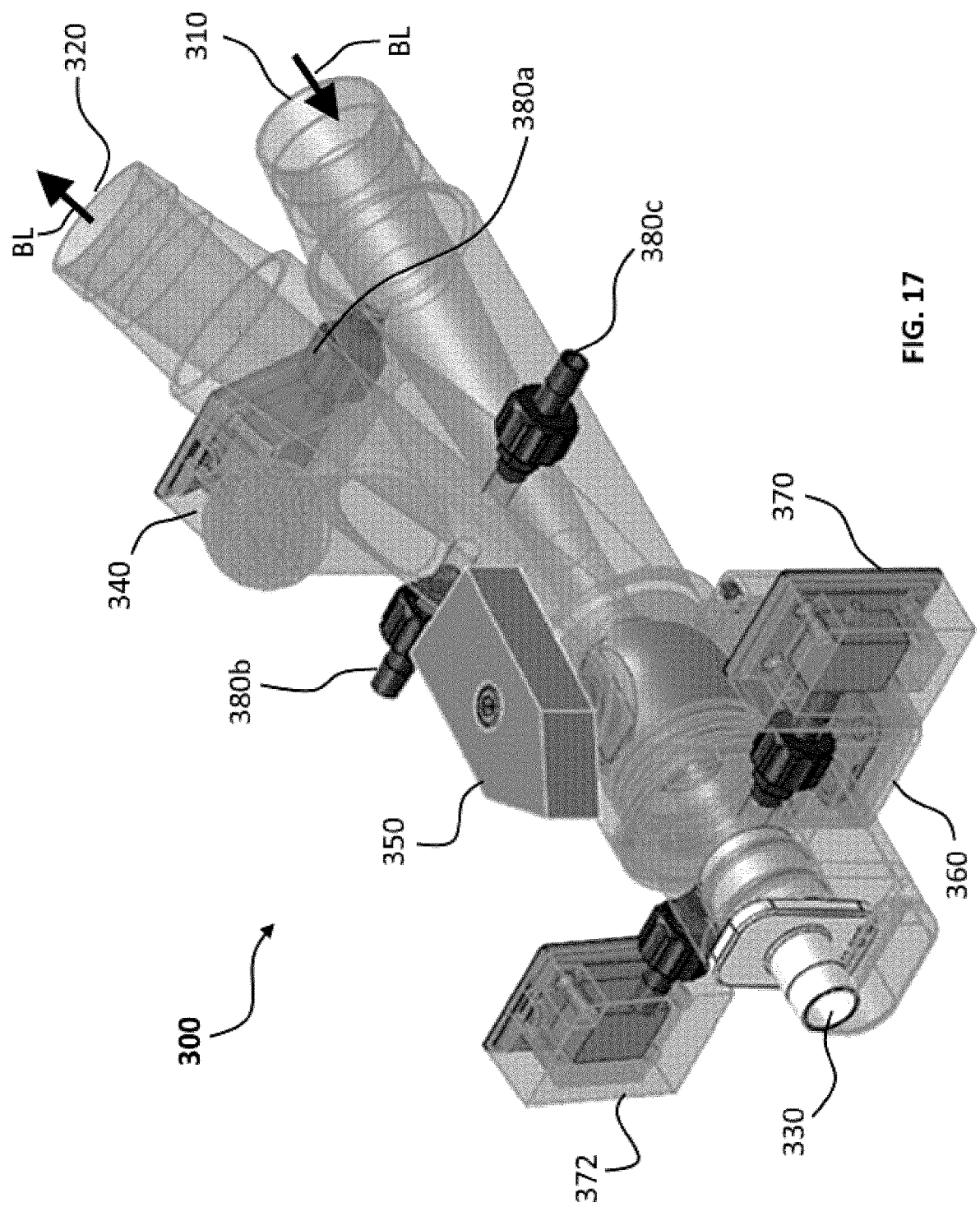
FIG. 17 shows a detailed perspective view of a Y-connector according to an embodiment of the present invention.

For instance, FIG. 17 is a detailed perspective view of a Y-connector in accordance of a preferred embodiment of the invention. The Y-connector (300) comprises an inspiratory liquid port (310) for receiving the breathable liquid (BL), e.g. PFC, from the reservoir (110) and/or the oxygenator (120), an expiratory liquid port (320) for returning the BL to the oxygenator (120), an endotracheal tube port (330), ETT port, for connection of the endotracheal tube ETT (150), a BL temperature sensor (340), and a valve (350), such as a rotary valve, allowing an user to select TLV by connecting the liquid ports (310) and (320), to the ETT port (330). The rotary valve (350) is mechanically connected to a rotation sensor (360) in order to measure the state of the rotary valve (350). The ETT port (330) comprises a first parietal pressure sensor (370) to measure the parietal pressure P of the flow in the ETT port. A second measure of the parietal pressure can be obtained with a second pressure sensor (372) located in front of the first parietal pressure sensor (370). The temperature sensor (340) is connected to the Y-connector via different connecting ports, either located in the expiratory circuit (380a), the inspiratory circuit (380b, as represented on the FIG. 17), or connected to both the inspiratory and expiratory circuits (380c). The BL temperature sensor (340) and the parietal pressure sensors (370, 372) are operably connected to the ventilator control unit VCU (180).

As illustrated on FIGS. 3 and 6B, the ventilator further comprises a control unit (180) operatively connected to the pressure sensor (160) and the different elements of the pumping assembly (140) for controllably exchanging the breathable liquid between the oxygenator and the mammal's lungs while controlling the expiratory flow of the breathable liquid pumped out of the lungs. The control unit (180) comprises a processor (182) for effecting in real-time a pressure P calculated from the measured pressure, e.g. at the mouth of the mammal or patient. When the pressure P reaches a negative threshold indicating a collapse of the mammal's trachea, the processor (182) allows reducing in real-time the expiratory flow of the breathable liquid according to a factor R while pumping the breathable liquid out of the lungs during a given expiratory period of time in order to maintain a targeted end-expiratory breathable liquid volume, or EEBLV, in the mammal's lungs. For instance, the negative threshold of the pressure P is equal or inferior to about −50 cmFhO and the given expiratory period of time during which the pumping assembly pumps the breathable liquid out of the lungs allows removing at least 80% of the targeted tidal expiratory volume of the breathable liquid. Preferably, the EEBLV is typically between 10 and 20 ml/Kg for a respiratory frequency of between 2 and 8 bpm (breath per minute), preferably 4 to 6 bpm, and a tidal volume of breathable liquid of between 4 to 10 mL/Kg. More details are presented in the examples of the present description.

According to a preferred embodiment, the control unit (180) is a computer equipped with a processor (182), a graphic user interface or GUI (184) for entering data and displaying measurements, traces and results, and a ventilator control unit in real-time or VCU (186). Pumps, valves and sensors of the ventilator are operatively connected to the processor.

Optionally, the reservoir (110) of the ventilator as illustrated on FIG. 6A is fluidly connected to the pumping assembly, and is preferably located at a level below the mammal or patient to take advantage of the gravitational force or gravity. Reference can be made to the table or surface on which the mammal or human is laid on during the ventilation procedure. The control unit (180) may be then further configured to open in real-time the pumping the respiratory circuit when the pressure P reaches a critical pressure inferior to about −130 cmEhO or superior to about +130 cmEhO. When the circuit is opened, the breathable liquid can be evacuated from the lungs by gravity towards the reservoir (110). Optionally, the ventilator may then further comprise an alarm unit (190) operatively connected to the control unit for triggering an alarm when the critical pressure is calculated by the processor of the control unit.

As illustrated on FIG. 1 or 6B, the ventilator (100) may further comprise a cooling unit (200) operatively connected to the oxygenator (120) for cooling and/or maintaining a temperature of the breathable liquid going through the oxygenator before being driven to the reservoir and going through the pumping assembly and mammal's lungs. Any sort of cooling units known in the art of liquid ventilation can be used with the ventilator (100). As illustrated on FIG. 6B, the cooling unit (200) can be a container or bath 210 having a upper access door 212 to allow pouring water into the container. The cooling unit can be controlled by a bath control system 214, preferably operatively connected to the control unit of the ventilator, as better explained herein after.

Any sort of breathable liquid known in the art of liquid ventilation, such as TLV, can be used with the ventilator (100). Preferably, the liquid (BL) is a perfluorocarbon or PFC.

Figure 21:
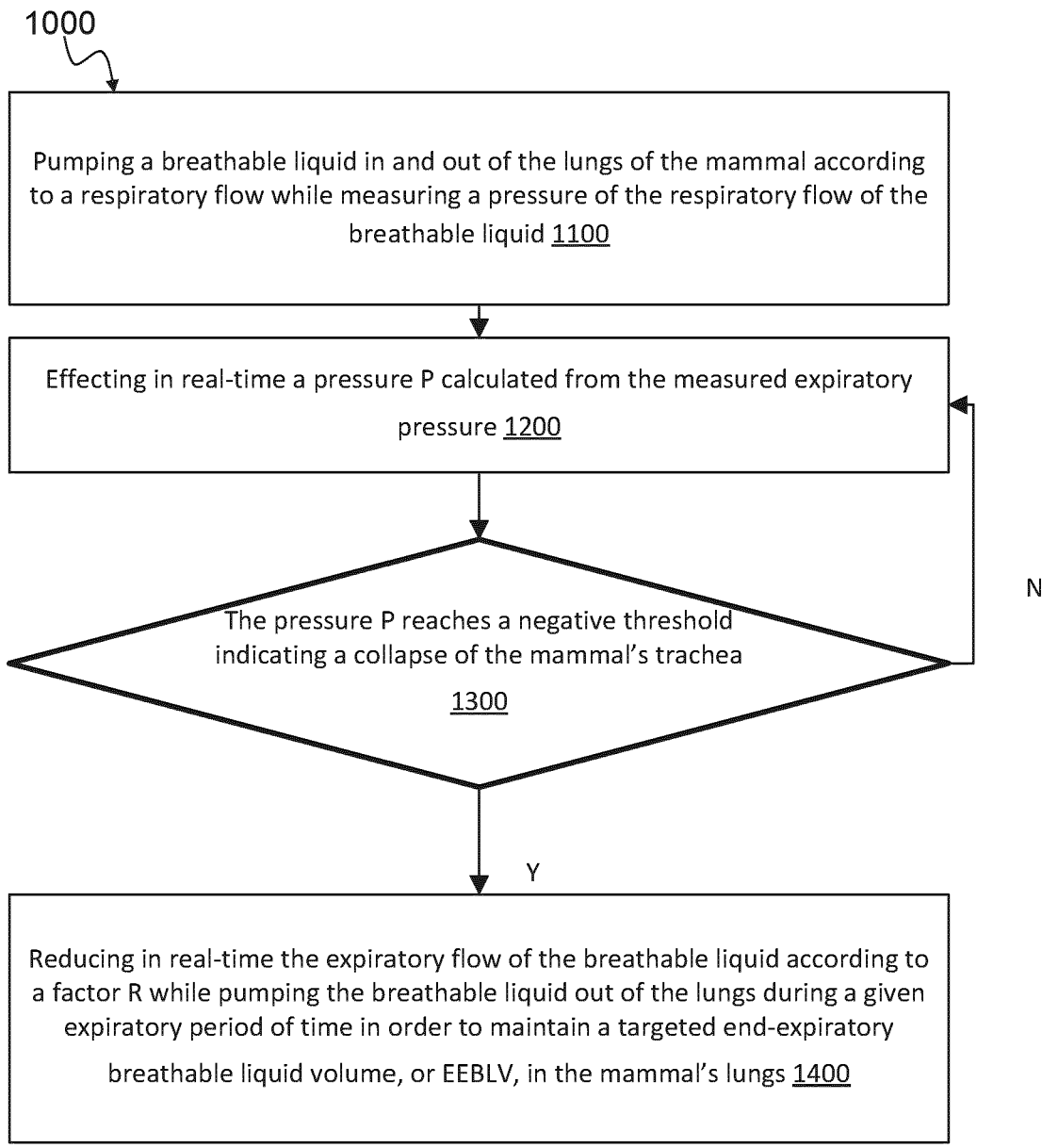
FIG. 21 is a sequence diagram showing operations of an exemplary method for liquid ventilation of a mammal according to an embodiment of the present invention.

As illustrated in FIG. 21, the present invention is directed to method (1000) for liquid ventilation of a mammal comprising the steps of:
  a) pumping a breathable liquid in and out of the lungs of the mammal according to a respiratory flow while measuring a pressure of the respiratory flow of the breathable liquid (1100);
  b) effecting in real-time a pressure P calculated from the measured expiratory pressure (1200); and
  c) when the pressure P reaches a negative threshold indicating a collapse of the mammal's trachea (1300), reducing in real-time the expiratory flow of the breathable liquid according to a factor R while pumping the breathable liquid out of the lungs during a given expiratory period of time in order to maintain a targeted end-expiratory breathable liquid volume, or EEBLV, in the mammal's lungs (1400).

According to a preferred embodiment, the EEBLV is between 10 and 20 ml/Kg for a respiratory frequency of between 2 and 8 rpm and a tidal volume of breathable liquid of between 4 and 10 mL/Kg.

Figure 22:
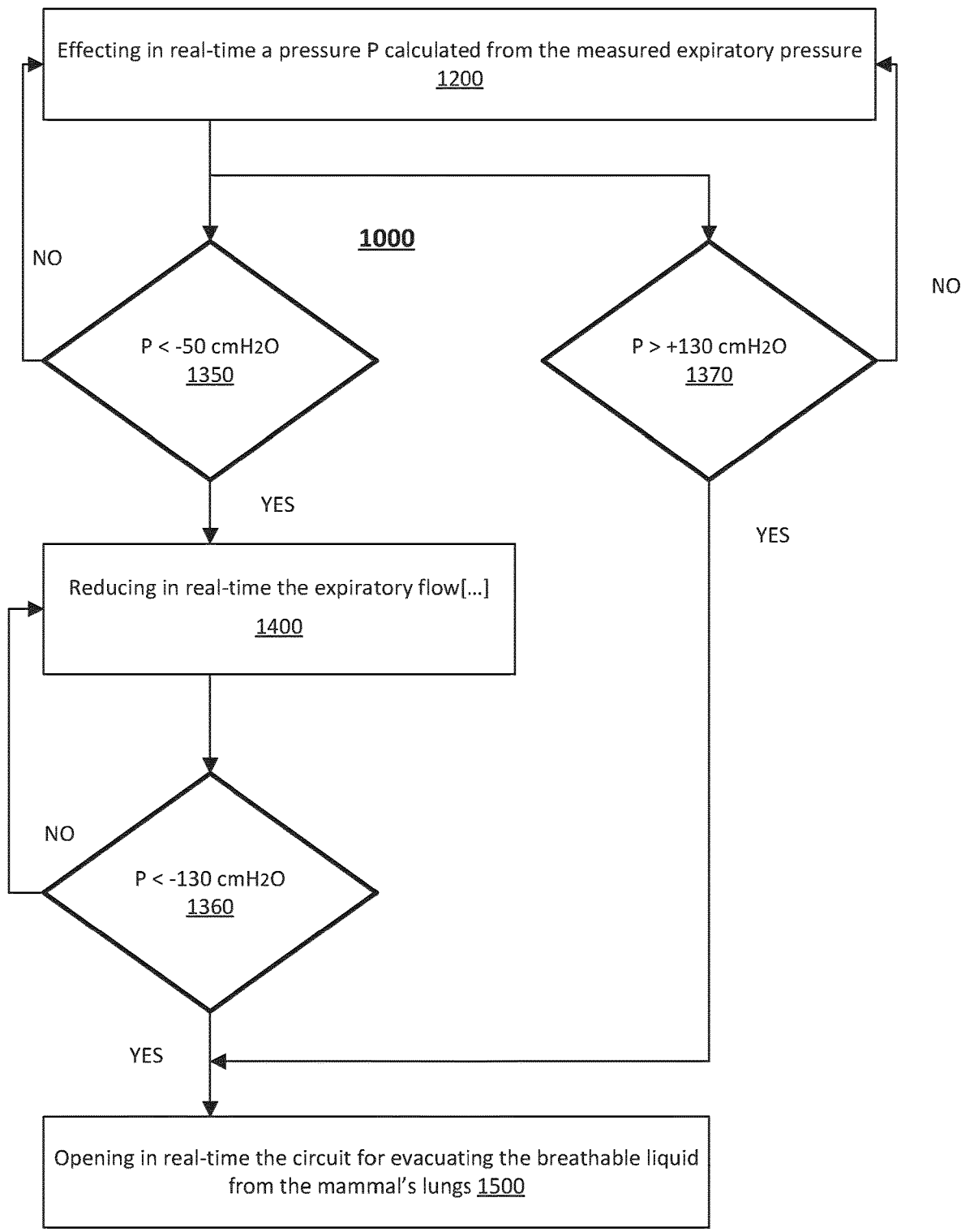
FIG. 22 is another sequence diagram showing operations of an exemplary method for liquid ventilation of a mammal according to an embodiment of the present invention.

According to the preferred embodiment illustrated on FIG. 22, the negative threshold of the pressure P is equal or inferior to about −50 cmEhO (1350), and the given expiratory period of time during which the breathable liquid is pumped out of the lungs allows removing at least 80% of the tidal volume of the breathable liquid.

According to anther preferred embodiment illustrated on FIG. 22, the method (1000) further comprises the step of evacuating the breathable liquid from the mammal's lungs (1500) when the pressure P is a critical value inferior to about −130 cmFhO (1360) or superior to about +130 cmFhO (1370. In that case, the method may further comprises the step of triggering an alarm when the critical value is reached.

According to a preferred embodiment, the method (1000) further comprises the step of cooling and/or maintaining a temperature of the breathable liquid while pumping the breathable liquid in and out of the lungs of the mammal. Preferably, the step of cooling and/or maintaining the temperature of the breathable liquid comprises:

producing a cooling fluid, and
thermally exchanging the cooling fluid with the breathable liquid for cooling the breathable liquid before re-instilling the breathable liquid into the mammars lung.

According to a preferred embodiment, the method (1000) further comprising the steps of:
  measuring an expiratory temperature of the breathable liquid pumped out of the mammal's lungs; and
  adjusting a temperature of the cooling fluid in function of the measured expiratory temperature for adjusting the temperature of the breathable liquid pumped into the lungs.

According to a preferred embodiment, the step of adjusting the temperature of the cooling fluid, such as PFC, consists in maintaining a flow of the cooling fluid during a first pre-set period of time, or stopping said flow during a second pre-set period of time, when the cooling fluid thermally exchanges with the breathable liquid.

Figure 2:
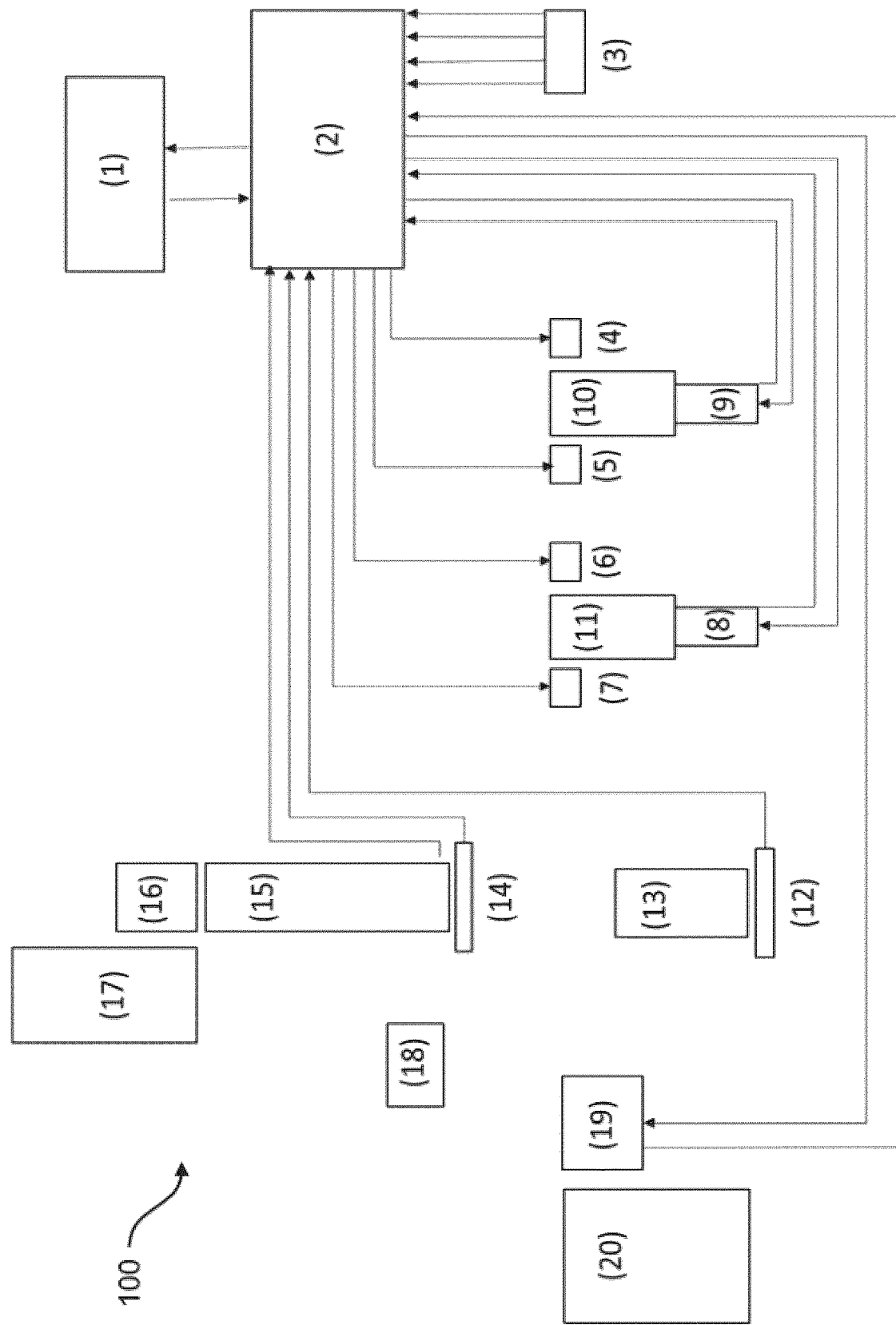
FIG. 2 is diagram illustrating a ventilator according to another embodiment of the present invention.

FIG. 2 schematically represents the different components of a ventilator equipped with a cooling unit in accordance with a preferred embodiment of the invention, and in which:
  (1) GUI: Graphic user interface for entering data and displaying measurements, traces and results;
  (2) VCU, ventilator control unit in real-time;
  (3) Y connector to patient with temperature sensor, two pressure sensors for the VCU and position sensor for rotative valve; optionally, temperature and pressure sensors with large dynamic for video switching unit— VSU—and indicator lights;
  (4-7) 4 binary valves, preferably binary normally open electrochemical valves, with state feedback (on/off);
  (8) expiration: motorization with absolute measurement of the piston head position;
  (9) inspiration: motorization with absolute measurement of the piston head position;
  (10) cylinder and pump head, inspiration, at the same level as the valves;
  (11) cylinder and pump head, expiration, at the same level as the valves;
  (12) scale for measuring the volume of PFC in (13);
  (13) buffer reservoir placed under the level of (3);
  (14) scale for measuring the volume of PFC in (15);
  (15) oxygenator equipped with a temperature sensor; (16) particulate filter that can retain PFC emissions;
  (17) gravity filler or bag;
  (18) manual gas mixer;
  (19) circulating pump for circulating heat transfer fluid equipped with a temperature sensor; and
  (20) heat exchanger.

Cooling Apparatus:

As aforesaid, another aspect of the present invention is directed to an apparatus for safe induction of hypothermia during liquid ventilation of a mammal, e g a human.

Figure 7:
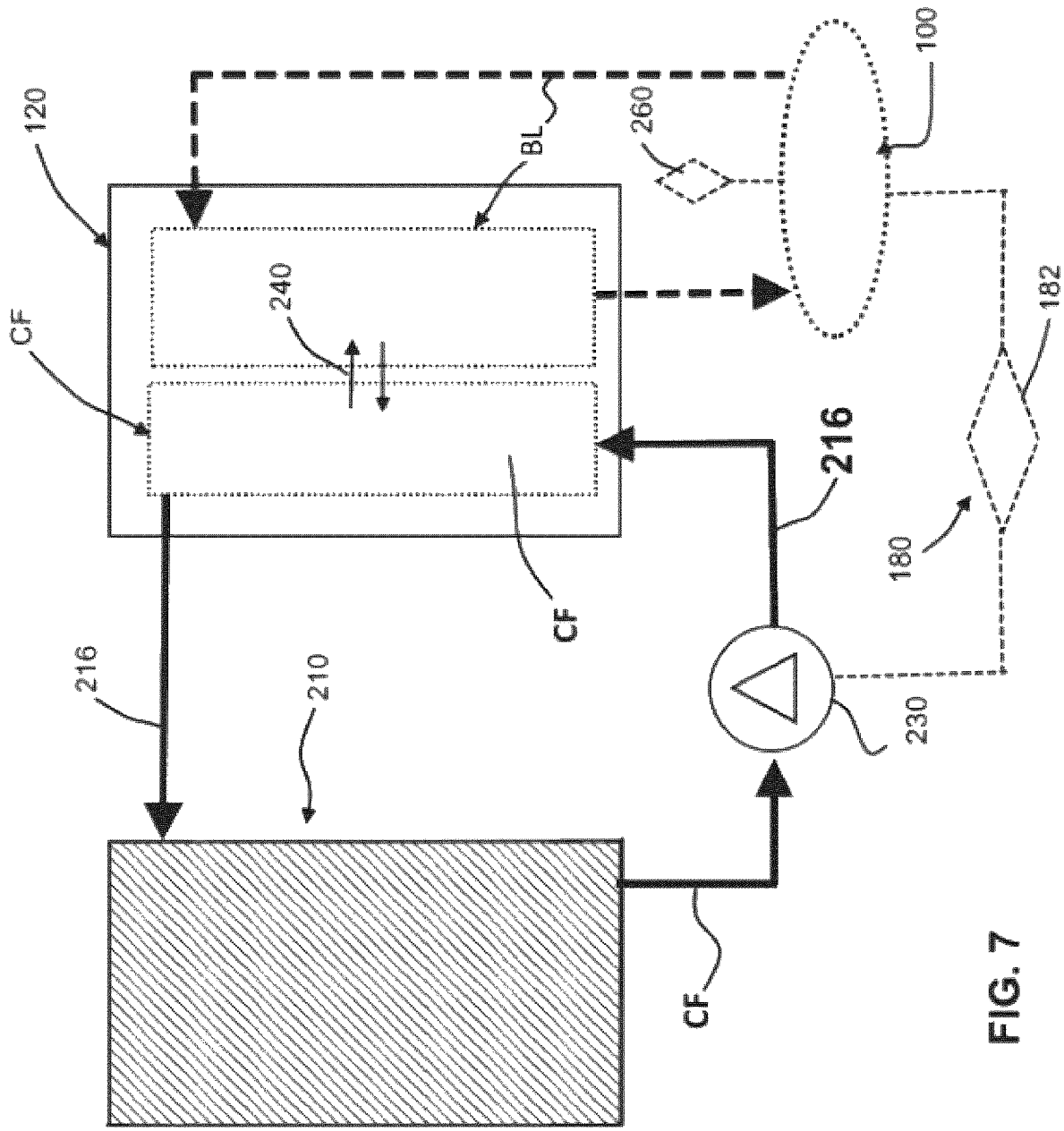
FIG. 7 illustrates an apparatus for safe induction of hypothermia during liquid ventilation of a mammal according to an embodiment of the present invention.

As illustrated on FIG. 7, the apparatus (200) comprising a cooling unit (210) configured to produce a cooling fluid (CF) at a cooling temperature when the cooling fluid circulates through the cooling unit. The cooling fluid may comprise water, preferably cold water at a temperature, preferably between −10° C. and +20° C., and all values in between. The cooling unit being in fluid communication (216) with an oxygenator (120) of a liquid ventilator (100) for receiving the cooling fluid therefrom (216). The apparatus also comprises a controllable pumping unit (230) in fluid communication with the oxygenator (120) and the cooling unit (210). The controllable pumping unit (230) is configured to pump back the cooling fluid (CF) from the cooling unit to the oxygenator module (120) where the cooling fluid (CF) thermally exchanges (240) with a breathable liquid (BL) of the liquid ventilator (100) circulating in the oxygenator module for controlling an inspiratory temperature of the breathable liquid oxygenated by the oxygenator before the re-instillation of the cooled oxygenated breathable liquid into the mammal's lung. The breathable liquid typically comprises perfluorocarbons, or PFC. The liquid ventilator (100) comprises a temperature sensor (260) for measuring in real-time an expiratory temperature of the breathable liquid pumped out of the mammal's lungs, the temperature sensor being operatively connected to the controllable pumping unit (230) to modify a flow of the cooling fluid and therefore to adjust the inspiratory temperature of the breathable liquid in function of the measured expiratory temperature.

FIG. 8(A) is an example of algorithm for the control of the pumping unit (230), which consists in turning on the pumping unit during a first pre-set period of time, e.g. 20 sec., and turning off the pumping unit during a second pre-set period of time, e.g. 30 sec., to control the flow of cooling liquid going through the cooling unit and the oxygenator. FIG. 8(B) is an example of how the control unit controls the pumping assembly to reach and maintain a target temperature of the expiratory flow around 31° C.

Alternatively, the pumping unit can be configured to pump the cooling fluid at a controlled mass flow rate in order to control a cooling power of the thermal exchange in the oxygenator. The pump is then operatively connected to a processor module of the liquid ventilator configured to control the mass flow rate of the cooling fluid and as such to vary the temperature of the breathable liquid in the oxygenator.

Figure 23:
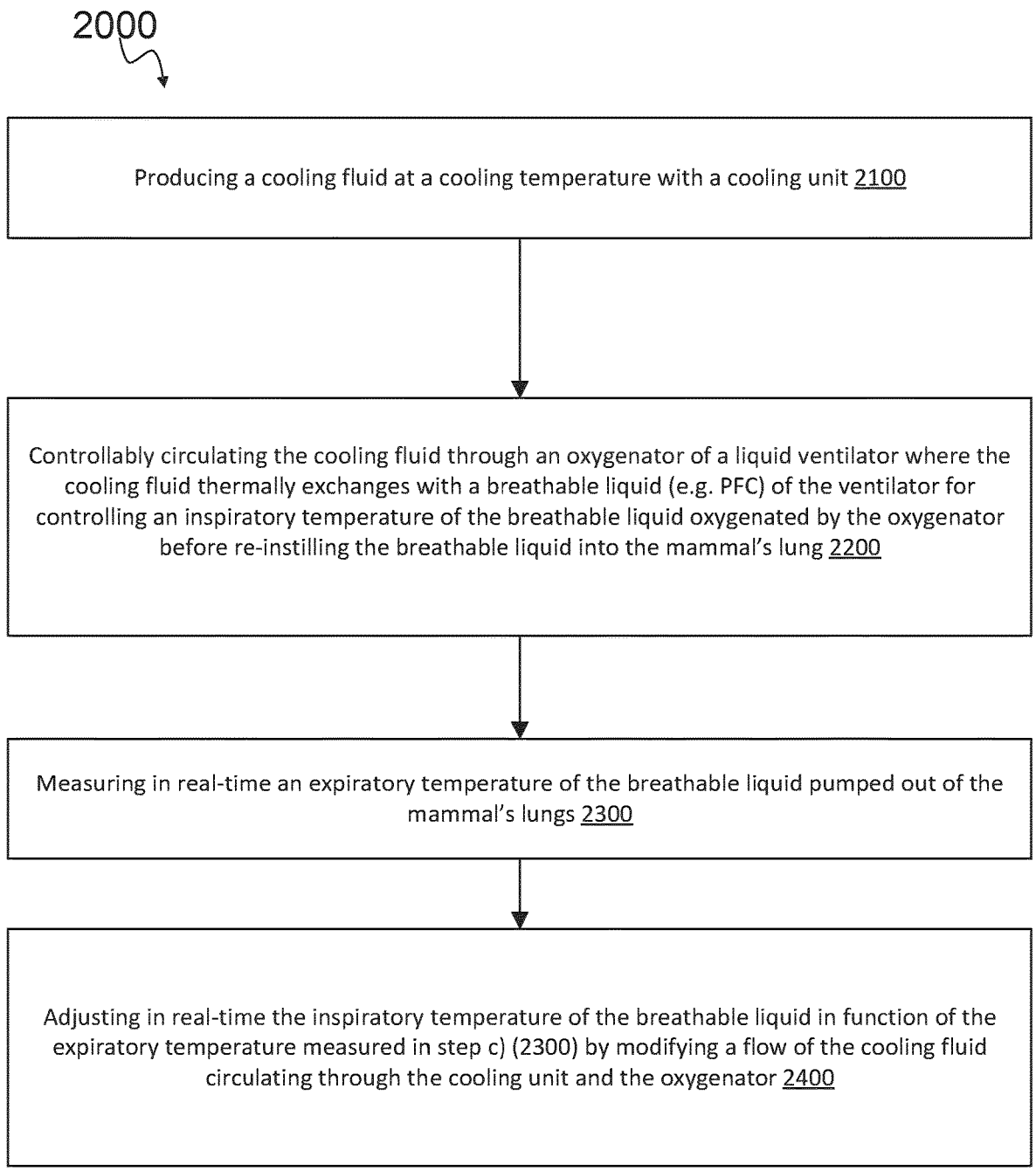
FIG. 23 is a sequence diagram showing operations of an exemplary method for safe induction of hypothermia during liquid ventilation of a mammal according to an embodiment of the present invention.

A method for induction of hypothermia in a mammal, such as a human, is illustrated on FIG. 23. The method (2000) comprises the steps of:
a) producing a cooling fluid at a cooling temperature with a cooling unit (2100);
b) controllably circulating the cooling fluid through an oxygenator of a liquid ventilator where the cooling fluid thermally exchanges with a breathable liquid (e.g. PFC) of the ventilator for controlling an inspiratory temperature of the breathable liquid oxygenated by the oxygenator before re-instilling the breathable liquid into the mammal's lung (2200);
c) measuring in real-time an expiratory temperature of the breathable liquid pumped out of the mammal's lungs (2300); and
d) adjusting in real-time the inspiratory temperature of the breathable liquid in function of the expiratory temperature measured in step c) (2300) by modifying a flow of the cooling fluid circulating through the cooling unit and the oxygenator (2400).

Figure 8:
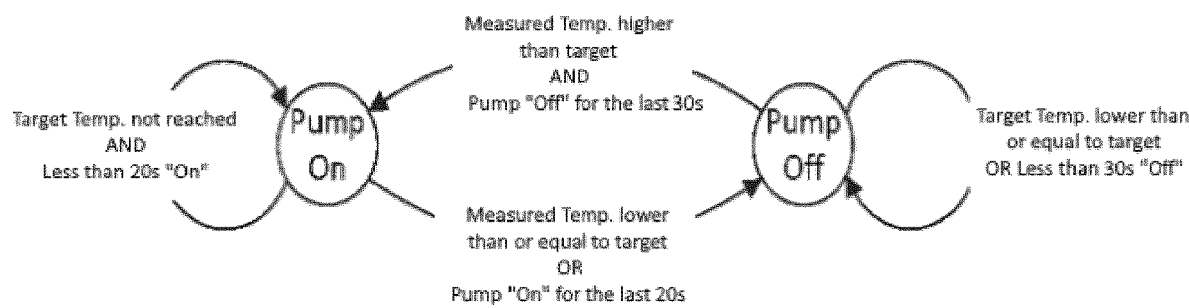
FIG. 8 illustrates the working of the pumping assembly of the apparatus illustrated on FIG. 7 with (A) the algorithm and (B) an example temperature control of the expiratory flow by controlling the pumping unit.
Figure 8:
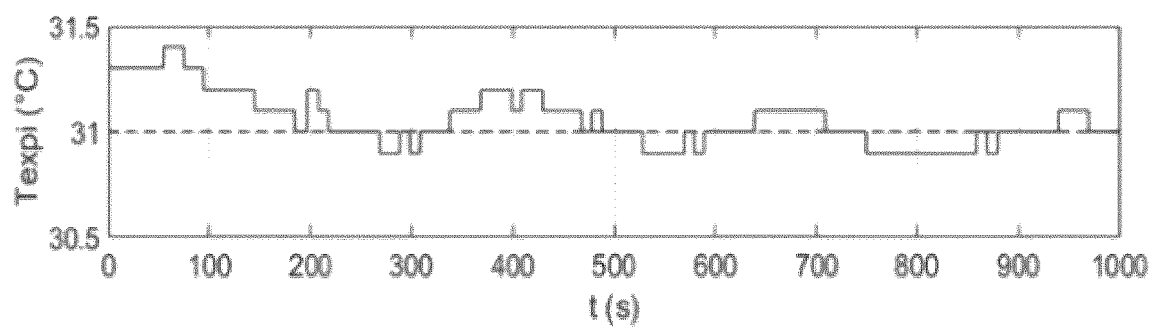
Figure 8:
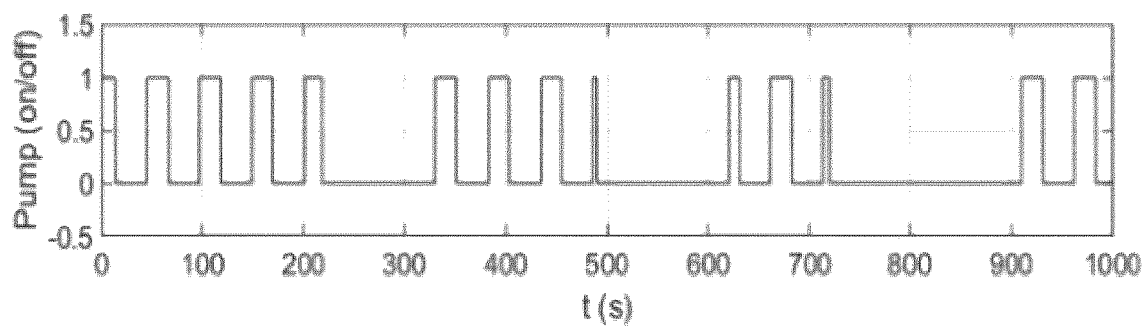

Preferably, the step of modifying the flow of the cooling fluid circulating through the cooling unit and the oxygenator (2400) consists in circulating the cooling fluid during a first pre-set period of time, e.g. 20 s, and stopping the circulation of the cooling liquid during a second pre-set period of time, e.g. 30 s, as illustrated on FIG. 8.

Alternatively, the method may further comprise the step of varying a mass flow rate of the cooling liquid circulating into the oxygenator for controlling a cooling power of the thermal exchange in the oxygenator. Preferably, the method (2000) then further comprises the step of varying the temperature of the breathable liquid circulating in the oxygenator by varying the mass flow rate of the cooling liquid circulating in the cooling unit.

EXAMPLES

Figure 9:
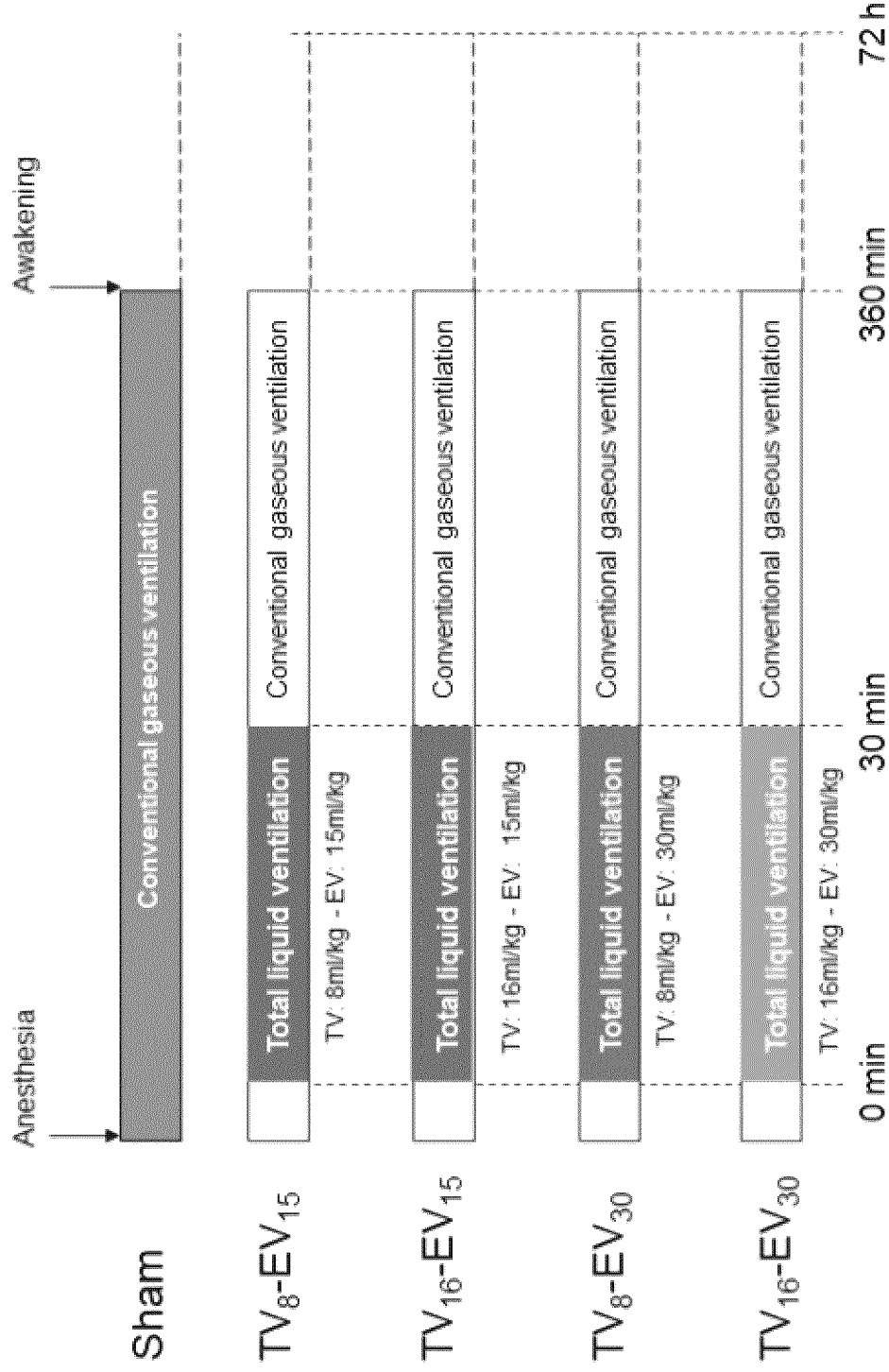
FIG. 9 illustrates an experimental protocol according to an embodiment of the present invention including five groups of piglets submitted to 30 min of TLV with different tidal volumes (TV of 8 or 16 ml/kg) and end-expiratory volumes (EEBLV of 15 or 30 ml/kg), as compared to Sham animals with conventional mechanical ventilation only, the four corresponding groups are so-called TVs-EVu, TVie-EVis, TV8-EV30 and TV16-EV30, respectively.

Acute Effects of Total Liquid Ventilation with Different Conditions of Lung Filling In preliminary experiments, lung volume has been assessed by chest computerized tomography (CT-scan) in four anesthetized piglets. Lung end-expiratory volume achieved 13.8±1.8 ml/kg and 37.7±8.8 ml/kg at PEEP=0 and 5 cmEhO, respectively. It is consistent with previous findings showing physiological FRC in the middle of this range, around 25-30 ml/kg in babies. Accordingly, we decided to evaluate the effect of TLV with end-expiratory volumes of PFC (EEBLV) close to these "extreme" physiological volumes, i.e., below or close to estimated FRC at either 15 or 30 ml/kg, respectively. A dedicated device for small animals, as illustrated on FIG. 1, was used. TLV was induced with perfluoctylbromide (PFOB) TLV. As illustrated in FIG. 9, the evaluation of the two selected EEBLV levels was crossed with two different levels of tidal volume (TV) set at either 8 or 16 ml/kg (TVs-EVis, TVie-EVis, TVs-EV30, TV16-EV30 groups, respectively). In all groups, animals were submitted to 30 min of TLV (n=5 in each group), with respiratory rate fixed to maintain similar respiratory minute volume in all groups (i.e., 9 vs 4.5 cycles in the groups with TV=8 or 16 ml/kg, respectively). An additional group of Sham animals were submitted to conventional gas ventilation without TLV (n=5).

As shown in Table 1 A and 1B herein after, the target EEBLV of 15 and 30 ml/kg were maintained throughout TLV in the corresponding groups. Surprisingly, end-expiratory static pressure was negative in the two groups with EEBLV set at 15 ml/kg, as compared to +6-8 cmFhO in the groups filled with 30 ml/kg of EEBLV. This peculiar finding can be explained by the active exhalation driven by the piston pump during TLV. In the TVs-E Vis and TV8-EV30 groups, this led to slight depression and could suggest that the actual EEBLV was yet below FRC. End-inspiratory alveolar pause pressure also increased along with TV and EEBLV in the different groups, achieving a maximal value ~20 cmFhO in TV8-EV30. Blood oxygenation and pH were not significantly modified during TLV in the different groups vs Sham animals.

TABLE 1A

End-expiratory pressure (cml⁻O) and volume of liquid (ml/kg)

| Parameters | Group | mean and standard error of the mean (sem) | Time during TLV (min) | | | | | |
|---|---|---|---|---|---|---|---|---|
| | | | 5.0 | 10.0 | 15.0 | 20.0 | 25.0 | 30.0 |
| End-expiratory pressure (cmH20) | TV8-EV15 | mean | 1.5 | −1.5 | −2.0 | −0.8 | −0.6 | −1.0 |
| | | sem | 1.1 | 1.3 | 1.0 | 1.1 | 1.1 | 0.9 |
| | TV8-EV30 | mean | 6.3 | 7.8 | 7.4 | 7.6 | 8.1 | 7.7 |
| | | sem | 1.4 | 0.7 | 0.8 | 0.4 | 0.6 | 0.8 |

TABLE 1A-continued

End-expiratory pressure (cmH2O) and volume of liquid (ml/kg)

| Parameters | Group | mean and standard error of the mean (sem) | Time during TLV (min) 5.0 | 10.0 | 15.0 | 20.0 | 25.0 | 30.0 |
|---|---|---|---|---|---|---|---|---|
| | TV16-EV15 | mean | 0.1 | −0.8 | −1.1 | −1.6 | −1.5 | −1.2 |
| | | sem | 2.2 | 1.3 | 1.4 | 0.7 | 0.8 | 0.9 |
| | TV16-EV30 | mean | 6.8 | 7.8 | 7.2 | 7.5 | 7.1 | 6.7 |
| | | sem | 2.2 | 3.0 | 2.5 | 2.7 | 2.5 | 2.7 |
| End-inspiratory pressure (cmH20) | TV8-EV15 | mean | 8.0 | 7.3 | 8.1 | 6.8 | 6.8 | 6.9 |
| | | sem | 0.9 | 1.6 | 1.3 | 1.0 | 0.9 | 1.0 |
| | TV8-EV30 | mean | 16.9 | 16.3 | 15.6 | 15.7 | 16.0 | 15.0 |
| | | sem | 1.1 | 1.1 | 0.9 | 0.7 | 1.1 | 0.9 |
| | TV16-EV30 | mean | 14.7 | 14.4 | 12.7 | 12.8 | 12.3 | 11.9 |
| | | sem | 1.3 | 1.4 | 1.7 | 1.1 | 1.2 | 1.0 |
| | TV16-EV30 | mean | 19.3 | 20.7 | 22.2 | 18.7 | 18.3 | 18.3 |
| | | sem | 2.4 | 2.3 | 1.5 | 2.4 | 2.2 | 2.2 |
| End-expiratory volume of liquid (ml/kg) | TV8-EV15 | mean | 16.5 | 17.0 | 17.8 | 17.8 | 17.2 | 17.8 |
| | | sem | 2.0 | 2.1 | 2.1 | 1.9 | 0.9 | 1.3 |
| | TV8-EV30 | mean | 31.4 | 32.1 | 30.7 | 31.8 | 31.3 | 29.2 |
| | | sem | 2.7 | 0.7 | 0.9 | 1.9 | 1.1 | 1.1 |
| | TV16-EV15 | mean | 16.9 | 17.3 | 16.2 | 16.6 | 16.9 | 18.3 |
| | | sem | 1.5 | 1.0 | 1.2 | 1.2 | 1.5 | 2.2 |
| | TV16-EV30 | mean | 29.3 | 31.9 | 31.9 | 31.9 | 32.4 | 31.1 |
| | | sem | 1.4 | 0.6 | 0.9 | 0.9 | 1.2 | 0.9 |

TABLE IB

Blood partial pressure (mmHg)

| | | | Baseline | TLV | 360 min post tlv |
|---|---|---|---|---|---|
| P02 (mmHg) | TV8-EV15 | mean | 209.2 | 156.2 | 184.0 |
| | | sem | 19.4 | 28.4 | 47.3 |
| | TV8-EV30 | mean | 204.2 | 173.4 | 187.0 |
| | | sem | 25.1 | 58.1 | 53.7 |
| | TV16-EV15 | mean | 203.0 | 203.4 | 159.2 |
| | | sem | 8.0 | 37.0 | 9.9 |
| | TV16-EV30 | mean | 193.8 | 195.6 | 104.8 |
| | | sem | 10.1 | 43.2 | 19.5 |

Animal Recovery after Total Liquid Ventilation

As illustrated on FIG. 9, after the episode of 30 min of TLV, the piglets were submitted to 5 h of conventional mechanical ventilation, after which they were weaned from ventilation and awakened. Oxygen enrichment was permitted during 24 hours using semi-hermetic cages. After return to spontaneous breathing, gas exchange and hemodynamic parameters were not significantly modified in animals previously submitted to TLV vs Sham A non-significant decrease in p02 was observed in TV16-EV30 as compared to other groups. Yet, two animals of this very group rapidly presented severe acute respiratory failure after awakening. They were euthanized and gross post-mortem analysis showed macroscopic lung congestion and hemorrhage.

The days after TLV, animals from the TVs-EVis. TV16-EV15 and TV8-EV30, groups did not show any sign of respiratory dysfunction as compared to Sham. These animals were followed during 3 days with no sign of acute respiratory discomfort. Conversely, respiratory discomfort and dyspnea were observed in the three surviving animals from the TV 16-EV30 group. Respiratory rate achieved 145±9 breaths/min after 24 h, as compared to 41±8 breaths/min in Sham animals (p<0.05). Two animals were euthanized for persistent polypnea after 24 h in the TV16-EV30 group and the last one after 48 h following TLV, respectively.

The histological examinations of the lungs confirmed severe pulmonary alterations in the TV16-EV30 as compared to all other groups. Indeed, we observed normal appearance in the Sham, TVs-EVis, TVie-EVis and TV8-EV30 groups. We only observed non specific foci of infection in some areas. In the TV16-EV30, we observed typical alterations of diffuse alveolar damage including severe alveolitis, alveolar hemorrhage and hyaline membranes. Some areas showed alveolar or bronchiolar dilation with a typical "balloon-like" pattern compatible with overdistension in the latter group.

Technology Up-Scale for Automatized TLV in Large Animals

Figure 10:
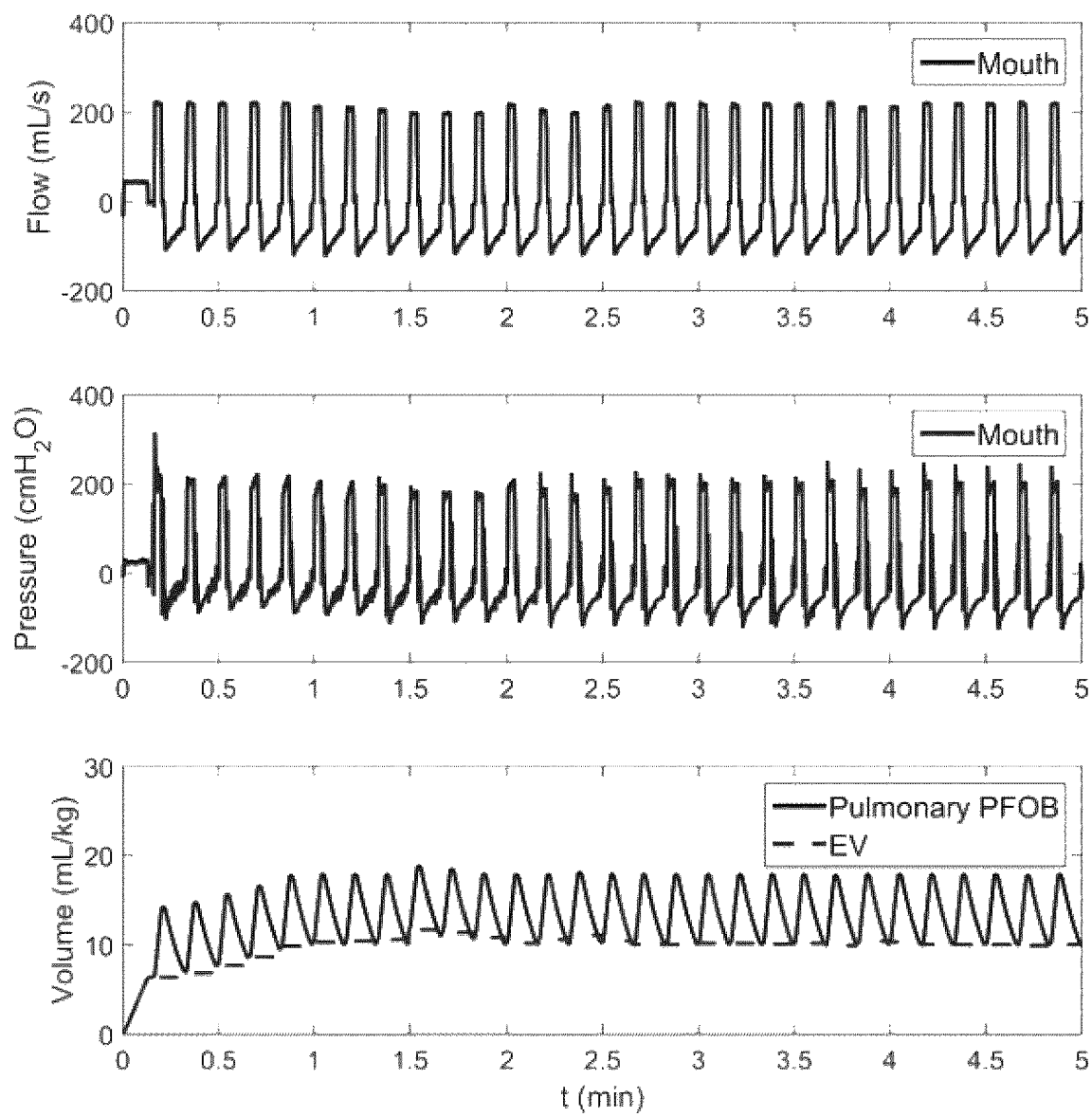
FIG. 10 shows typical perfluorocarbon flow (upper raw), pressure at mouth and pulmonary volume of perfluorocarbon during the first 5 min of total liquid ventilation (TLV) in a 63 kg pig.

The previous experiments showed that lung-conservative approach of TLV could provide safe TLV with full benefits in both physiological and pathophysiological conditions in piglets. One would argue that those findings could not be extrapolated in large animals due to higher body mass, chest size and lung maturity. Accordingly, the liquid ventilator has been up-scaled and a technology has been designed for large animals up to 100 kg. All the components were adapted with specific materials for medical applications (FIGS. 5, 6A and 6B). In addition, the TLV process as been automatized. A specific algorithm has been developed to estimate the volume of liquid into the lungs and maintain EEBLV at a given target, as it was demonstrated to be a critical parameter. Thereby, expiratory TV was continuously and automatically modified by the ventilator to exactly maintain the EEBLV set by the investigator (FIG. 10). Similarly, PFC initial temperature and rewarming rate was calculated, as our main goal was here to use TLV for the induction of rapid hypothermia.

Total (or tidal) liquid ventilation (TLV) necessitates a dedicated mechanical system in order to ventilate completely filled lungs with a tidal volume of breathable liquid (BL). The liquid ventilator inserts and withdraws the tidal volume Vtof BL from the lungs in order to ensure that the amount of breathable liquid in the lungs at the end of expiration phase (EEBLV) is closed to the targeted EEBLV specified by the clinician. The measurement of EEBLV can be obtained by monitoring the patient's weight, end-expiratory pressure or liquid volume in the ventilator. For this purpose, the volume of BL in the oxygenator may be measured using a scale (114) (see FIG. 6A) located under the oxygenator (120) for measuring the weight of the oxygenator. Another method is to instrument the oxygenator with a pressure sensor or a liquid float sensor in order to measure the level of BL in the oxygenator, and so on to calculate the volume of BL in the ventilator. For each respiratory cycle indexed, k, the end-expiratory breathable liquid volume, EEBLV[k], is calculated by the ventilator control unit (VCU) via the measurement of the BL located in the oxygenator (V oxygenator), the knowledge of the primary volume of BL (Vprim) (the initial volume of BL in the liquid ventilator before the TLV) and the volume of BL in the two pumps. If the ventilator (100) comprises a reservoir (110), a second scale (112) can located under the reservoir can be used for the same purpose.

The control unit module computes the EEBLV correction, \VIk I. according to the measured EEBLV, noted EEBLV[k], and the targeted EEBLV, noted EEBLVref[k]:

$$AV[k]=(EEBLVref[k]-EEBLV[k])$$

where k is the index of the cycle. The requested correction of EEBLV, AV[k\, is the BL volume to retrieve from (if negative) or to add into (if positive) the lungs during one cycle. The targeted inspiratory and expiratory volume is computed with the targeted tidal volume, Vt[k\, and the requested correction A V[k\.

If EEBLV needs to be decreased, if AF[ ]<0, the next inspired liquid is V,\k+1 1 V,\k\-|AF[&]|

If EEBLV needs to be increased, if AF[V]>0, the next expired liquid is Ve[k+1]=Vt[k]-|AF[&]| The distinct advantage of our TLV prototype is its ability to control EEBLV using a system of independent pumps and the ability to estimate EEBLV via the measurement of BL volume in the reservoir and the measurement of BL in the two pumps.

Figure 18:
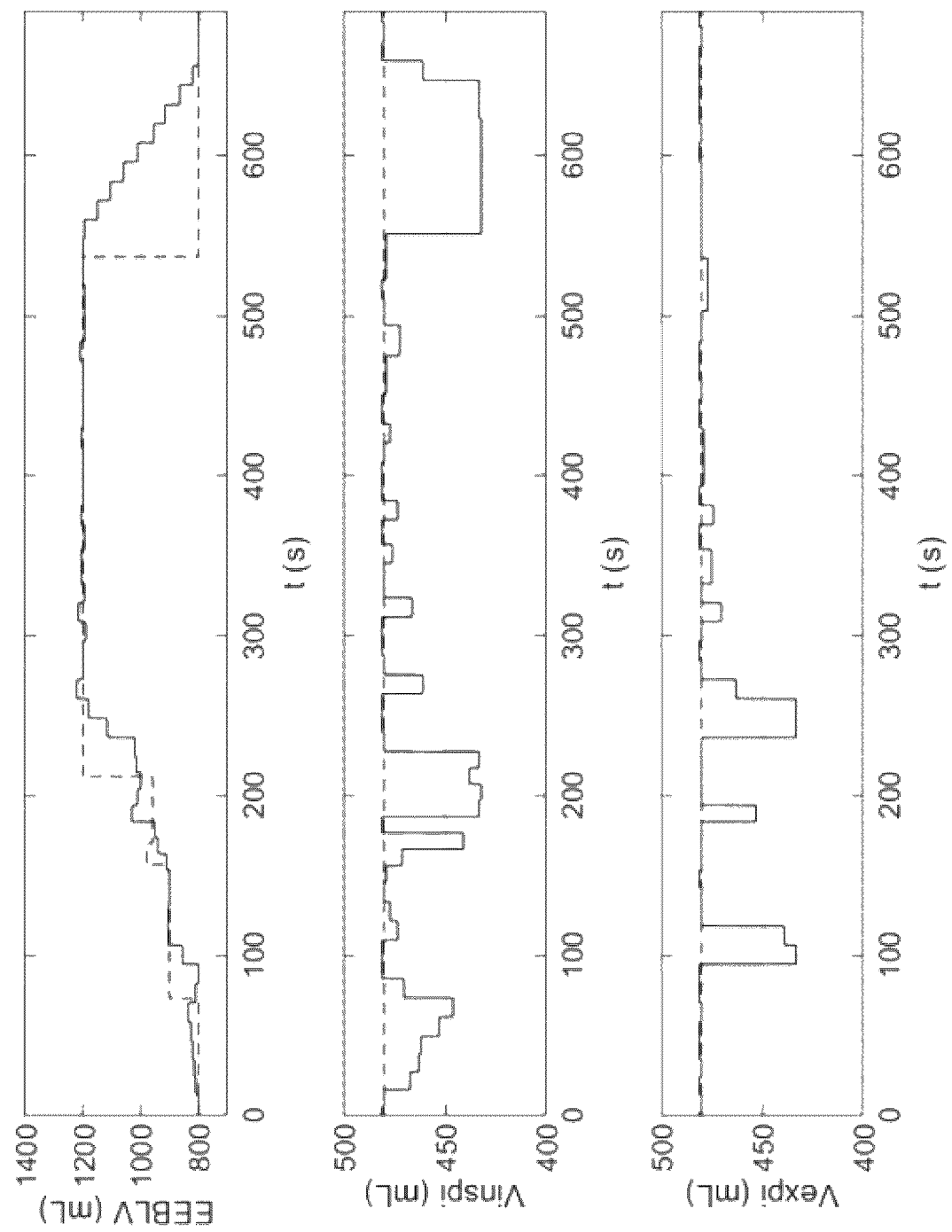
FIG. 18 shows the measure of EEBLV, inspired volume and expired volume during the liquid ventilation of a pig.

In accordance with the above, FIG. 18 shows as an example the measurements of the EEBLV (mL), the inspiratory volume Vinspi (mL) and the expiratory volume Vexpi (mL) during the ventilation of a pig (80 kg) from the time 17 minutes (1050 s) for 14.5 minutes:

Targeted Tidal volume: VT=6 mL/Kg (VT=480 mL for 80 Kg)
Targeted Frequency: F=6 bpm The EEBLV is estimated from the amount of liquid in the reservoir. The Modification of EEBLVref by the user: the user modify the value the EEBLVref in order to increase EEBLV from 10 mL/Kg to 15 mL/Kg (800 mL to 1200 mL) and after, the user decreases the EEBLVref from 15 mL/Kg to 10 mL/Kg. The inspired and expired liquid volumes are modulated (below the targeted tidal volume=480 mL) to reach the targeted EEBLV.

Figure 15:
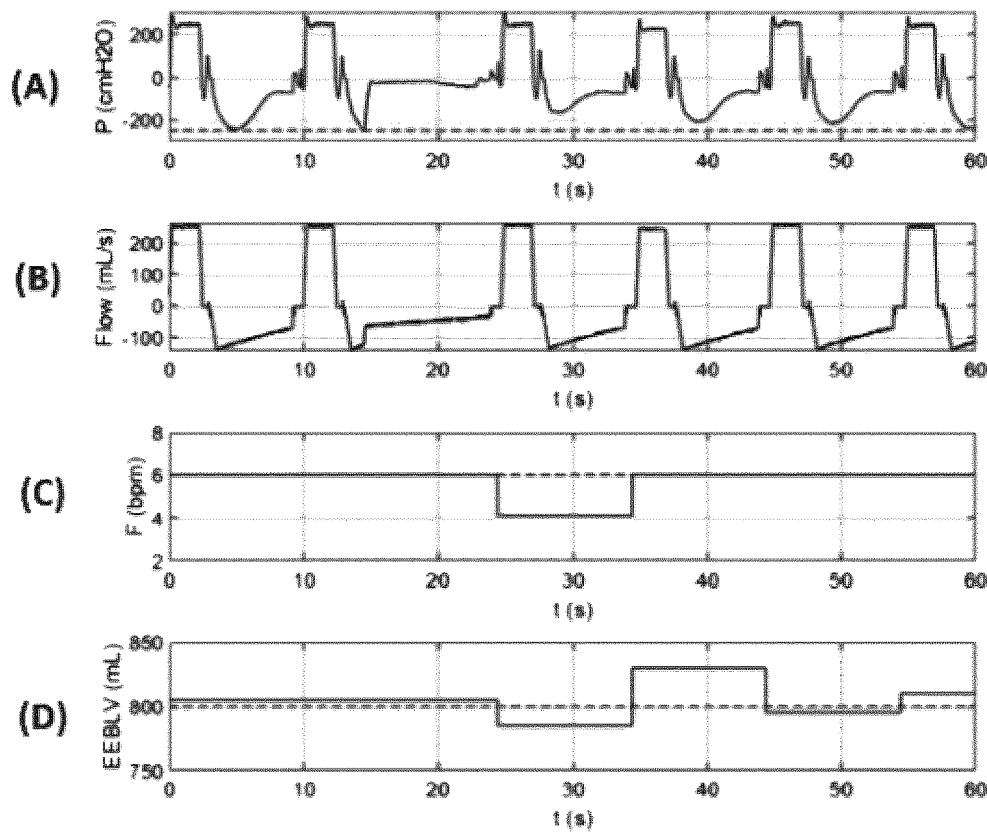
FIG. 15 shows respiratory cycles measurements in application of the method according to an embodiment of the present invention when a collapses phenomenon occurs: (A) pressure ($cmH2O$), (B) flow (mL/s), (C) frequency F (bpm), (D) EEBLV (mL)
Figure 16:
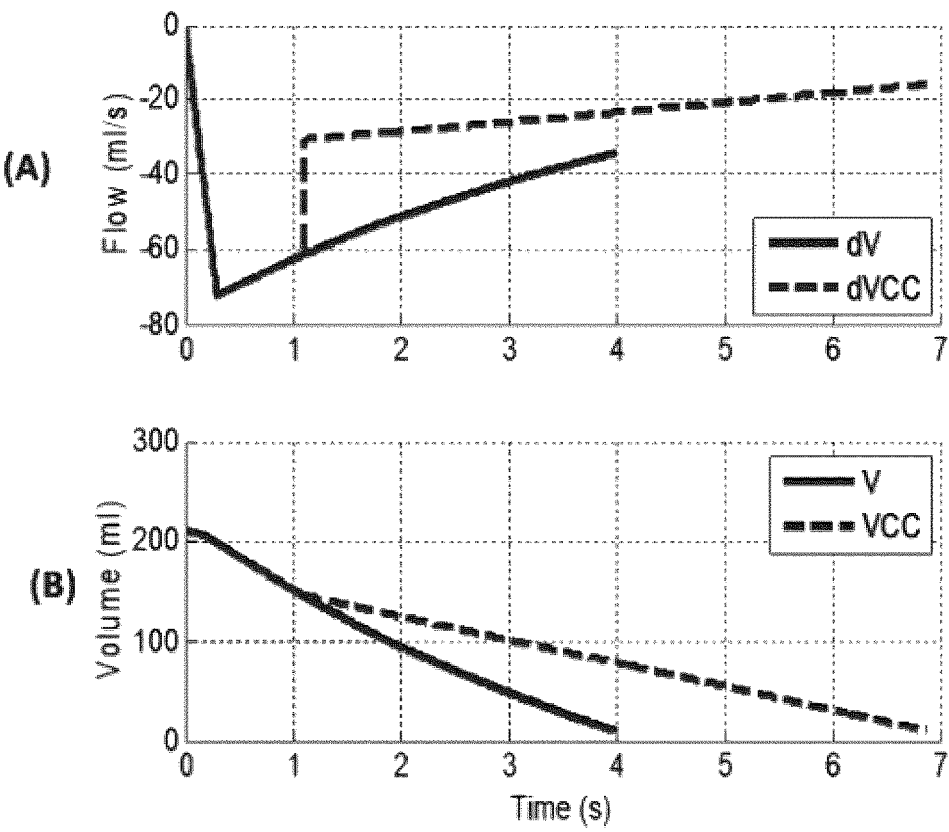
FIG. 16 shows normal flow and volume of breathable liquid in function of time versus when an airway collapse phenomenon occurs.

FIGS. 15 and 16 provides respiratory cycles data when a collapse of the trachea occurs. In particular, FIG. 15 shows an experiment with a pig of 73 Kg, using the up-scaled ventilator (FIGS. 5 and 6) during 60 s from the time 1450 s. The dashed line of pressure (FIG. 15 A) corresponds to the limit of collapse at −250 cmFhO, the dashed line of frequency (FIG. 15C) shows the targeted frequency at 6 bpm and the dashed line of EEBLV (FIG. 15D) shows the targeted EELV at 800 mL. Before about 15 s, the targets are reached: EEBLV=800 mL/Kg (10.9 mL/Kg) (FIG. 15D), Vt=585 mL (8 mL/Kg) (Flow FIG. 15C), F=6 bpm (FIG. 15C), with expiration time of 6 s. At the instant 15 s: we observe a detection in real-time of the collapse when the pressure reaches the threshold at −250 cmFhO, the expiratory flow is automatically reduced, in real-time, from −120 mL/s to −60 mL/s, to cease the airway collapse The remaining expiratory time is extended such that the extended expiration time period is about 1 1s. Hence, the respiratory frequency punctually lowers from 6 bpm to 4 bpm because of the extended expiration time (calculated at the instant 25 s). The EEBLV punctually lowers to 785 mL (instead of 800 mL). Despite this «accident», the EEBLV remains regulated around the target value of 800 mL. After 25 s, there is no more collapse FIG. 15A).

Now referring to FIG. 16, while an airway collapse phenomenon is happening, the pressure drop is measured at the Y-connector and the airway collapse is detected by the ventilator once the pressure reaches the airway collapse pressure limit. Once the airway collapse is detected by the ventilator, the expiratory flow is automatically reduced to cease the airway collapse, and thus to prevent a total airway collapse. The flow reduction is proportional to the reduction ratio of the airway collapse control RatioCC which is set by the user. If the airway collapse is happening during the exponential phase of the expiration, the remaining expiratory time is extended by a ratio equal to the inverse of RatioCC. Then, the expiratory flow profile is recalculated as a ramp down profile to complete the expiration of the tidal volume. If the airway collapse is happening before the exponential phase, the expiratory time is not modified and the expiratory flow profile is reduced by a ratio equal to RatioCC. Moreover, once the airway collapse is detected, an alarm is activated to warn the operator that the ventilation parameters need to be adapted in order to prevent the airway collapse phenomenon on the next expiration.

Figure 19:
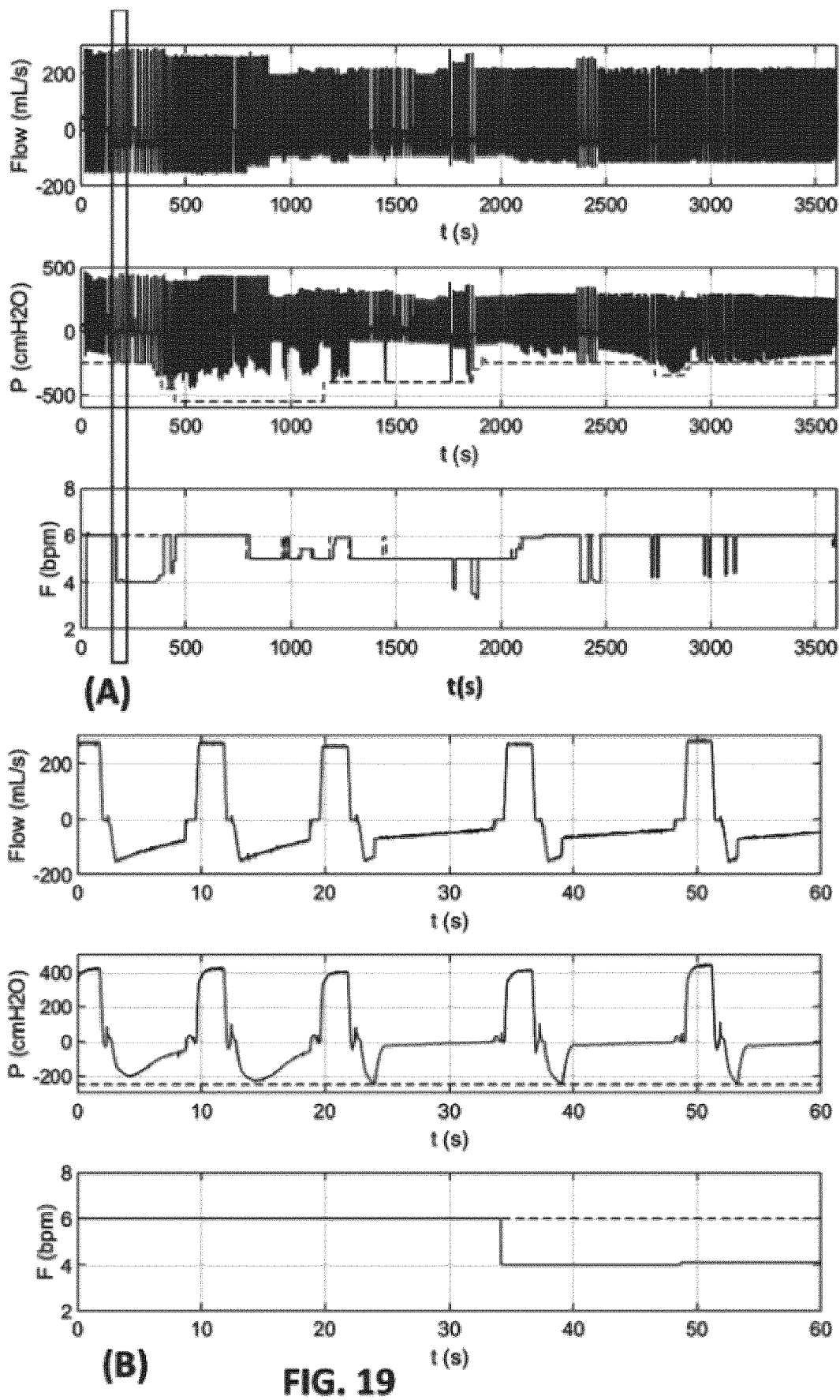
FIG. 19 shows signals measured on a pig during one hour of liquid ventilation (A) and the same signals during one minute from the time 2.3 minutes of the liquid ventilation (B)
Figure 20:
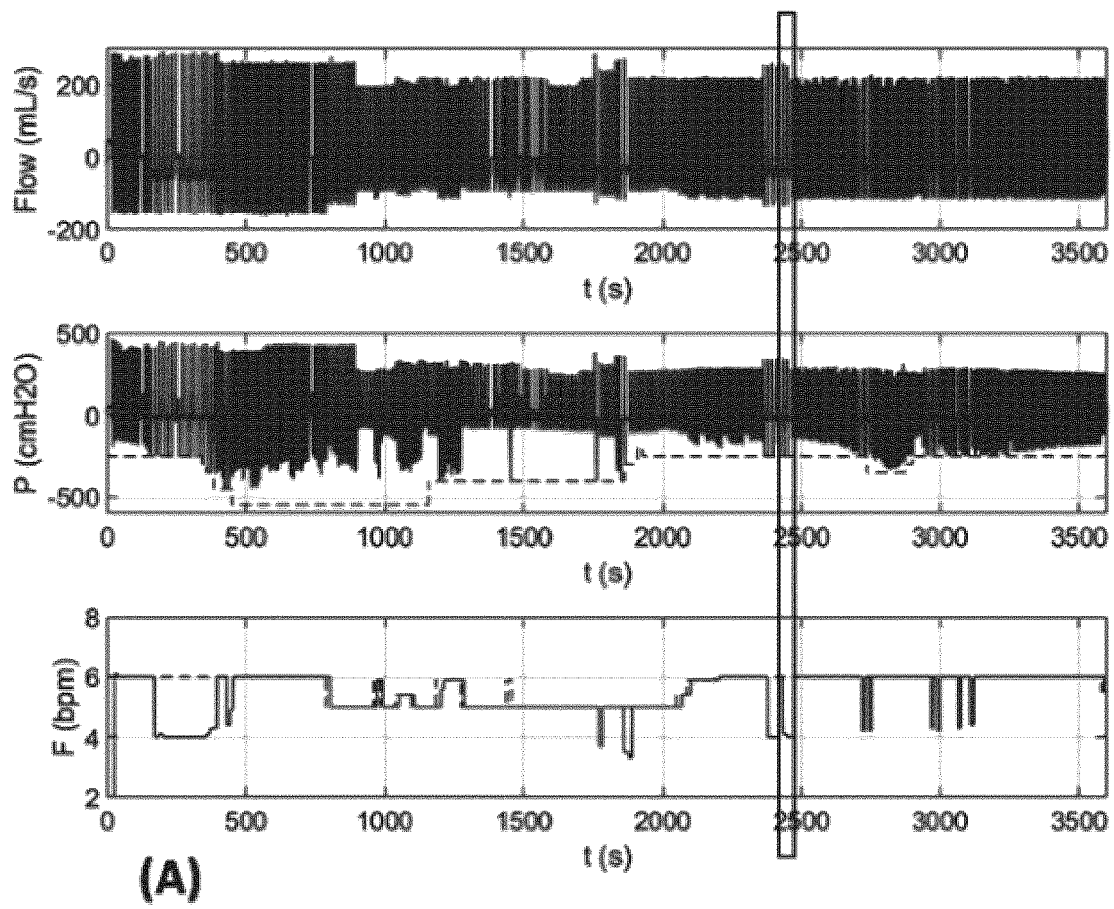
FIG. 20 shows the same signals as for FIG. 19 measured on a pig during one hour of liquid ventilation (A) and the same signals during one minute from the time 40.55 minutes of the liquid ventilation (B)

FIGS. 19 and 20 shows signals measured during one hour of liquid ventilation (A) on a pig (60-80 kg) using the up-scaled ventilator (FIGS. 5 and 6) and the same signals during one minute from the time 138 seconds (or 2.3 minutes) of the liquid ventilation (FIG. 19B) and during one minute from the time 2433 seconds (or 40.55 minutes) of the liquid ventilation. The flow estimated at the Y connector with the pumping system (mL/s): Positive value: inspiratory flow and negative value: expiratory flow (FIGS. 19A and 20 A). Pressure in cmFhO (FIGS. 19B and 20B) with plain line: pressure measured at the Y connector and dashed line: limit collapse set at different values. Instantaneous frequency F (in breath per minute or bpm) (FIGS. 19C and 20C) with plain line: F realized by the liquid ventilator, and dashed line: F desired frequency is set by the user.

FIG. 19B show the same signals during one minute from the time 2.3 minutes of the liquid ventilation. The dashed line of pressure corresponds to the limit of collapse set at −250 cmFhO, and the dashed line shows the desired frequency is set at 6 bpm. From 0 to 24 (s): normal liquid ventilation 3 cycles without collapse. The measured frequency (F) is equal to the desired frequency set at 6 bpm (cycle of 10 s). The expiratory profile allows to avoid the collapse, because the pressure measured at the Y-connector is below −250 cmFhO. The expiratory time is 7 s. The inspiratory time is 3 s. From 24 s to 60 s: 3 collapus are detected. At these moments, the pressure measured at the Y-connector is below −250 cmFhO (value set by the operator). At 24 s, the expiratory flow is automatically decreased from −140 mL/s to −70 mL/s and the expiratory time is increased to 1 1s. So, the estimated instantaneous frequency decreases from 6 bpm to 4 bpm (at time 34 s).

FIG. 20 shows signals measured during one minute from the time 40.55 minutes of the liquid ventilation. From 0 to 30 (s): collapus are detected. At these moments, the pressure measured at the Y-connector is below −250 crrdHO (value set by the operator). At 4.2 s, the expiratory flow is automatically decreased from −120 mL/s to −60 mL/s and the expiratory time is increased to 1 1s. So, the estimated instantaneous frequency is 4 bpm instead of the target 6 bpm. From 30 s: normal liquid ventilation without collapse because the pressure measured at the Y-connector is below −250 cmFhO. The expiratory time is 7 s. The inspiratory time is 3 s. So, the measured frequency (F) is equal to the desired frequency set at 6 bpm (cycle of 10 s).

Total Liquid Ventilation Using the Same Approach could Provide Ultrafast Cooling and Safety in Large Pigs.

Figure 11:
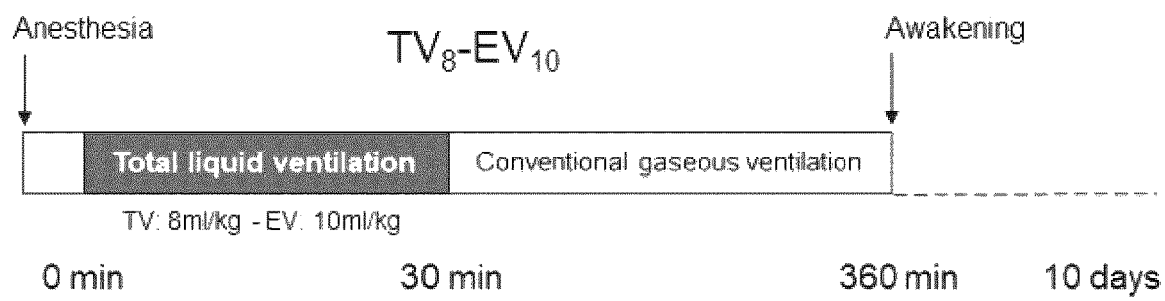
FIG. 11 is a schematic representation of experimental protocol in large pigs submitted to 30 min of hypothermic TLV followed by conventional gaseous ventilation and rewarming, before awakening. Animals were followed during 10 days before euthanasia for post-mortem analyses.
Figures 12, 13:
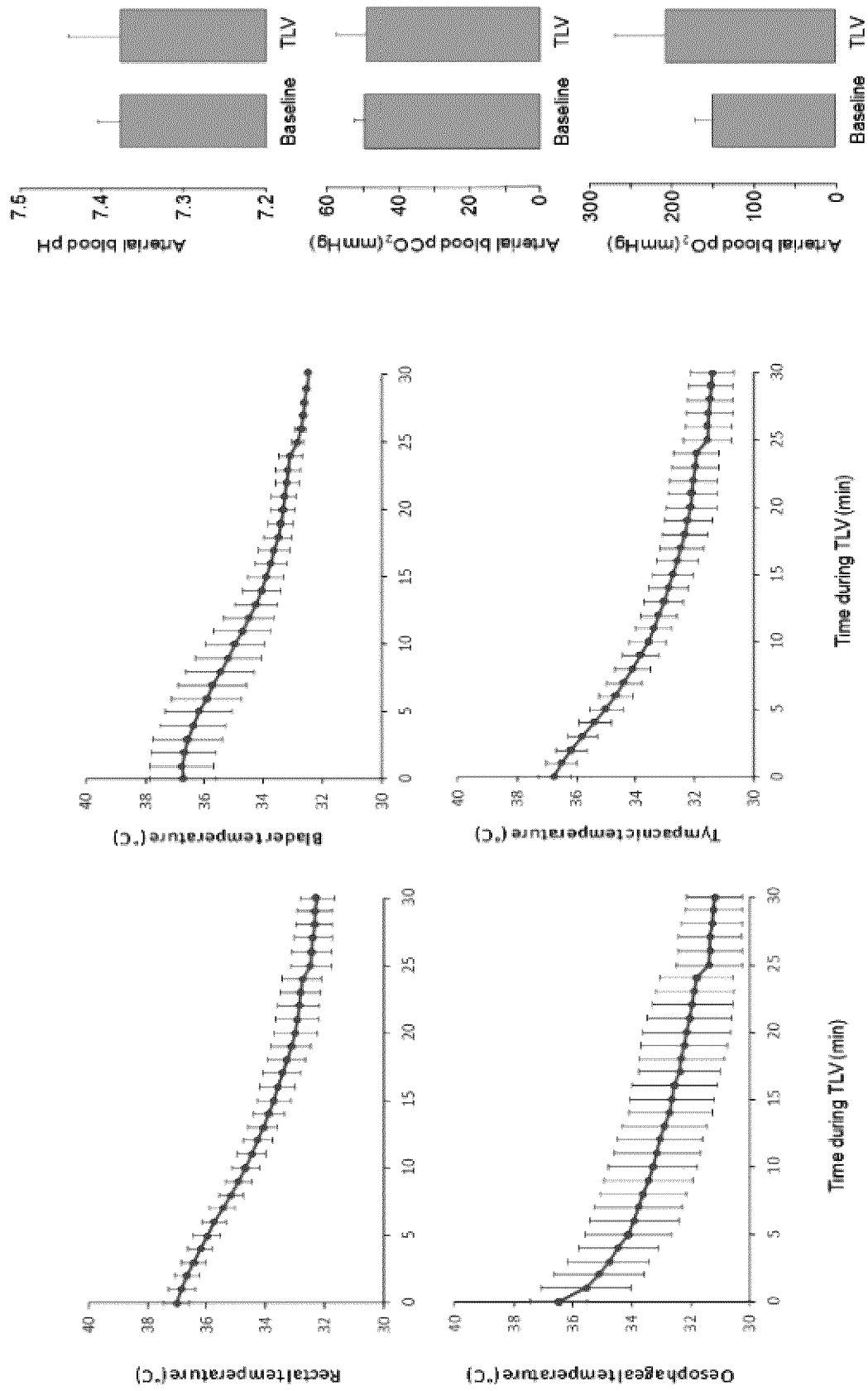
FIG. 12 shows body temperatures in the different compartments during the TLV episode, showing a rapid decrease of target temperature (32-33° C.) within 20 min in all compartments.
FIG. 13 shows blood pH, and carbon dioxide and oxygen partial pressure ($pCO_2$ and $pO3/4$ respectively)
Figure 14:
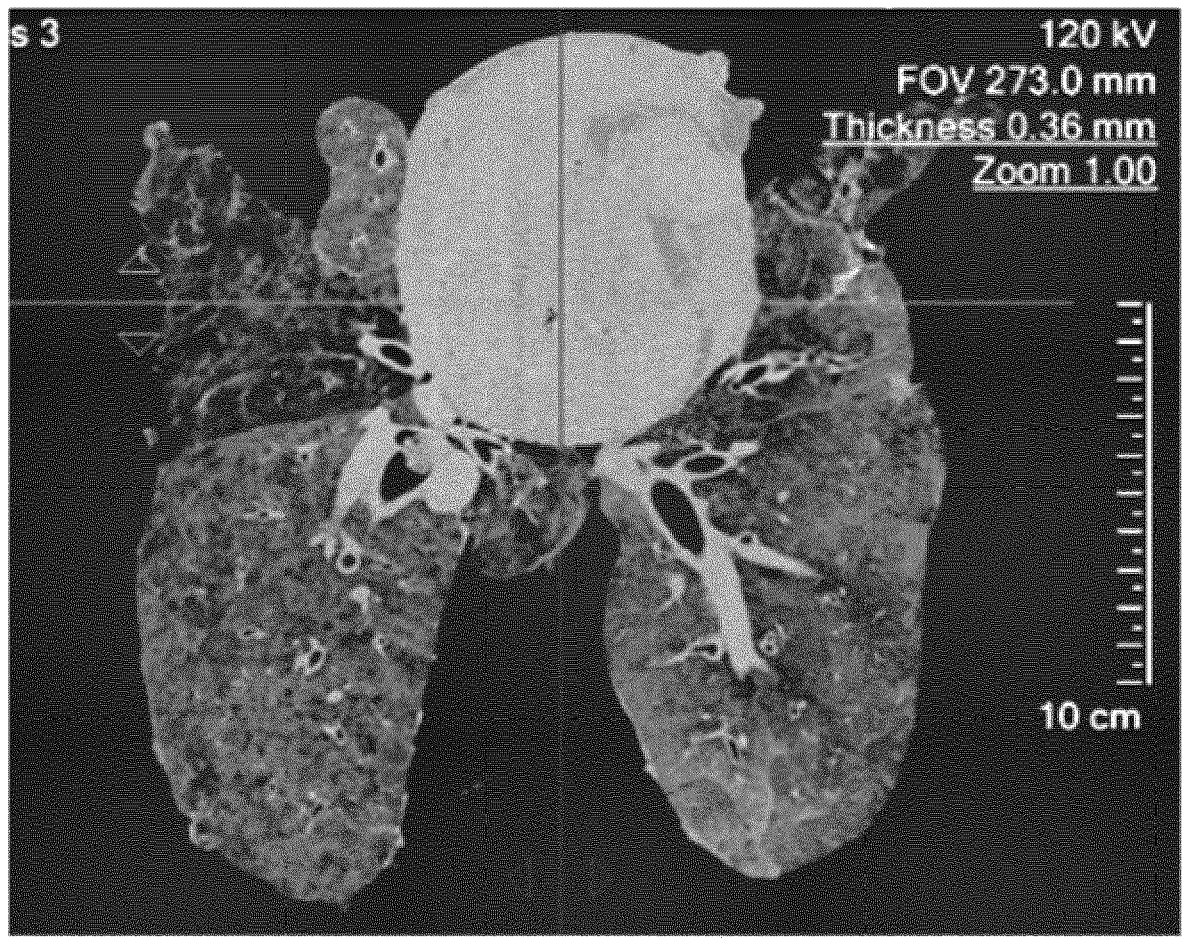
FIG. 14 shows thoracic computerized tomography (CT-scan) of an explanted lung in a pig at the end of the follow-up. No macroscopic foci of perfluorocarbons can be observed, suggesting complete elimination.

Relevant settings for TLV in large animals have been determined by preliminary experiments. As illustrated in FIG. 11, four pigs weighing 67±3 kg were submitted to 30 min of TLV with TV and EEBLV set at 8 and 10 ml/kg, respectively. It allowed maintaining EEBLV below FRC. The target temperature range of 31-33° C. was achieved within less than 20 min in the entire body (see FIG. 12). Gas exchanges were normal after 30 min of TLV as compared to baseline ventilation. After 30 min of TLV, animals resumed to conventional gas ventilation and were slowly rewarmed. They were weaned from ventilation within 4 to 6 h, after which they returned to the animal room without any oxygen supplementation. All animals presented an excellent recovery with no sign of respiratory discomfort. Pulmonary gas exchanges was not modified during TLV as compared to conventional mechanical ventilation, as shown by arterial blood pH and partial pressure of 02 and CO2 (FIG. 13). In addition, blood oxygen saturation remained above 97-98% in all animals from the first day after TLV to the end of the follow-up, showing a long-term pulmonary tolerance of the procedure. After 10 days, they were euthanized for lung harvesting. As illustrated in FIG. 14, CT-scan imaging of explanted lungs did not show any visible macroscopic foci of PFC residues since the entire lung parenchyma was diffusely hypoattenuating.

A new approach for TLV through incomplete lung filling with PFC below FRC and subsequent tidal liquid ventilation is disclosed. This represents a radical paradigm shift as compared to previous beliefs, that considered that lungs should be primarily completely filled with PFC and fully degassed since the filling phase. This lung-conservative approach of TLV was further automatized with an up-scaled device for large animals continuously controlling EEBLV below FRC ranges. Partial liquid ventilation was tested in humans but the largest trial raised skepticism regarding the actual safety of this procedure. Those negative results were poorly deciphered a posteriori and it was often overstated that any way of liquid ventilation enhanced trauma risks by itself, regardless its exact way of induction. Therefore, it was critical to evaluate lung mechanics precisely during TLV and its delayed consequences after resumption to spontaneous breathing. Here, we show that TLV could be induced safely when controlling EEBLV below expected FRC. This procedure was still able to provide ultra-fast cooling in piglets and large pigs, reinforcing previous results in small animals. This opens promising perspectives for target temperature management in cardiac arrest patients, beyond the other applications of liquid ventilation for lung lavage, drug delivery or lung imaging.

Until now, most reports with TLV were done in animal models of pediatric respiratory diseases with EEBLV and TV averaging 20-30 ml/kg and 15-30 ml/kg, respectively. The main rationale was that TLV could completely abolish the air-liquid interface and optimize pulmonary recruitment. However, the long-term pulmonary recovery was rarely evaluated after resumption to spontaneous breathing, which obviously often limited the translation of the results. Here, it has been showed that such approach could actually be deleterious and that incomplete filling with low EEBLV should be preferred, even if the air-liquid interface is not fully abolished in the initial phase. For instance, we have also conducted pressure-volume curves analyses, which demonstrated an inflexion point occurs around 40 ml/kg of liquid volume and 15 crrdUO of alveolar pressure, suggesting that beyond this point, hyperinflation and alveolar overdistension might happen. This could also bring possible explanations for the failure of partial liquid ventilation in patients with acute respiratory distress syndrome. Actually, the previously mentioned pivot trial tested the static intratracheal administration of 10 or 20 ml/kg of perflubron during conventional gas ventilation at PEEP=13 crrdUO and TV=8-10 ml/kg. This led to high end-inspiratory alveolar pressure averaging 30 crrdUO, which is far above the alveolar pressures observed in the present study. This could have led to very high lung volume that completely compromised the putative benefits of partial liquid ventilation. Overall, our finding suggests that the best-tolerated conditions of TLV are associated with a lung filling below FRC, which could be responsible for a certain level of derecruited alveoli in upper pulmonary regions. This alveolar reserve could allow subsequent and safe addition of tidal volume of liquid during liquid ventilation. A certain level of heterogeneity in liquid distribution at expiration could therefore be paradoxically more conservative.

An important finding is also that lung-conservative TLV exerts very fast cooling in both piglets and adults. This is the first study to confirm this finding in animals weighing up to 80 kg, further emphasizing the body-weight independent cooling rate of TLV. Such cooling was shown to provide potent neurological benefits after cardiac arrest in adult rabbits. In additional experiments, we also showed that benefits can also be observed in a neonatal model of cardiac arrest after hypoxic-ischemic encephalopathy. This supports the hypothesis of a very narrow therapeutic window of hypothermia after ischemic injury. In humans treated by therapeutic hypothermia, target temperature is usually achieved after at least 3-4 hours of cooling while TLV affords whole-body cooling in less than 30 min. Some techniques were shown to provide rapid regional cooling but TLV is able to cool the entire body rapidly, and not a single body compartment such as the brain with helmets or intrasinusal cooling.

Finally, a technological challenge has been overcome. For the first time, an automatized liquid ventilator able to perform TLV in large animals up to 80 kg has been developed and used. To inventor's knowledge, this is also the first demonstration of the pulmonary consequences of TLV in large animals after resumption to spontaneous breathing. This makes TLV a realistic strategy for further applications in humans.

In conclusion, it has been demonstrated that TLV with an accurate and reliable control of lung volumes of perilu orocarbons below FRC could provide the full potential of TLV in a novel and safe manner, despite incomplete initial degassing. This constitutes a paradigm shift through the "tidal" liquid ventilation of partly filled lungs, which strongly differs from the previously known TLV approach, opening promising perspectives for a safe clinical translation.

Those of ordinary skill in the art will realize that the description of the methods, ventilators and apparatus for inducing hypothermia are illustrative only and are not intended to be in any way limiting. Other embodiments will readily suggest themselves to such persons with ordinary skill in the art having the benefit of the present disclosure.

Furthermore, the disclosed methods, ventilators and apparatus for inducing hypothermia may be customized to offer valuable solutions to existing needs and problems of related to the lack of maturity of current liquid ventilation technology.

In the interest of clarity, not all of the routine features of the implementations of methods, ventilators and apparatus for inducing hypothermia are shown and described. It will, of course, be appreciated that in the development of any such actual implementation of the methods, ventilators and apparatus for inducing hypothermia, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of artificial ventilators having the benefit of the present disclosure.

Various network links may be implicitly or explicitly used in the context of the present invention. While a link may be depicted as a wireless link, it could also be embodied as a wired link using a coaxial cable, an optical fiber, a category 5 cable, and the like. A wired or wireless access point (not shown) may be present on the link between. Likewise, any number of routers (not shown) may be present and part of the link, which may further pass through the Internet.

The present invention is not affected by the way the different modules exchange information between them. For instance, the memory module and the processor module of the control unit could be connected by a parallel bus, but could also be connected by a serial connection or involve an intermediate module (not shown) without affecting the teachings of the present invention.

A method is generally conceived to be a self-consistent sequence of steps leading to a desired result. These steps require physical manipulations of physical quantities. Usually, though not necessarily, these quantities take the form of electrical or magnetic/electromagnetic signals capable of being stored, transferred, combined, compared, and otherwise manipulated. It is convenient at times, principally for reasons of common usage, to refer to these signals as bits, values, parameters, items, elements, objects, symbols, characters, terms, numbers, or the like. It should be noted, however, that all of these terms and similar terms are to be associated with the appropriate physical quantities and are merely convenient labels applied to these quantities.

The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses.

What is claimed is:

1. A method of use of a targeted end-expiratory breathable liquid volume, or EEBLV, of a breathable liquid inferior to a functional residual capacity, or FRC, of the lungs of a mammal for preventing deleterious effects on the mammal's lungs during a liquid ventilation of said mammal, during which a tidal volume of breathable liquid is added and removed at each respiratory cycle, said method comprising targeting the EEBLV of the breathable liquid inferior to the FRC of the lungs of the mammal while pumping a breathable liquid in and out of the lungs of the mammal.

2. The method of use of claim 1, wherein the EEBLV is between 10 and 20 mL/Kg for a respiratory frequency of between 2 rpm and 8 rpm and a tidal volume of the breathable liquid of 4 mL/Kg to 10 mL/Kg.

3. The method of use according to claim 1, wherein the breathable liquid comprises perflurocarbons or PFC.

4. The method of use according to claim 1, wherein the mammal is a human.

5. The method of use of claim 1, wherein the EEBLV is between 10 mL/Kg and 20 mL/Kg.

6. The method of use of claim 1, wherein the EEBLV is between 10 mL/Kg and 20 mL/Kg for a respiratory frequency of between 2 rpm and 8 rpm.

7. The method of use of claim 1, wherein the EEBLV is between 10 mL/Kg and 20 mL/Kg for a tidal volume of the breathable liquid of 4 mL/Kg to 10 mL/Kg.

8. A method for liquid ventilation of a mammal comprising the steps of:
   a) pumping a breathable liquid in and out of the lungs of the mammal according to a respiratory flow while measuring a pressure of the respiratory flow of the breathable liquid;
   b) effecting in real-time a pressure P calculated from the measured expiratory pressure; and
   c) when the pressure P reaches a negative threshold indicating a collapse of the mammal's trachea, reducing in real-time the expiratory flow of the breathable liquid to cease the airway collapse while pumping the breathable liquid out of the lungs during a given expiratory period of time in order to maintain a targeted end-expiratory breathable liquid volume, or EEBLV, in the mammal's lungs.

9. The method according to claim 8, wherein the EEBLV is between 10 mL/Kg and 20 mL/Kg for a respiratory frequency of between 2 rpm and 8 rpm and a tidal volume of breathable liquid of between 4 mL/Kg and 10 mL/Kg.

10. The method according to claim 8, wherein the negative threshold of the pressure P is equal or inferior to about $-50$ cm $H_2O$, and wherein the given expiratory period of time during which the breathable liquid is pumped out of the lungs allows removing at least 80% of the volume of the breathable liquid.

11. The method according to claim 8, further comprising the step of evacuating the breathable liquid from the mammal's lungs when the pressure P is a critical value inferior to about $-130$ cm $H_2O$ or superior to about $+130$ cm $H_2O$.

12. The method according to claim 8, further comprising the step of triggering an alarm when a critical value of pressure inferior to about $-130$ cm $H_2O$ or superior to about $+130$ cm $H_2O$ is reached.

13. The method according to claim 8, further comprising the step of cooling and/or maintaining a temperature of the breathable liquid while pumping the breathable liquid in and out of the lungs of the mammal.

14. The method according to claim 8, further comprising the step of cooling and/or maintaining a temperature of the breathable liquid while pumping the breathable liquid in and out of the lungs of the mammal, wherein the step of cooling and/or maintaining the temperature of the breathable liquid comprises: producing a cooling fluid, and thermally exchanging the cooling fluid with the breathable liquid for cooling the breathable liquid before re-instilling the breathable liquid into the mammal's lung.

15. The method of claim 8, further comprising the steps of:
measuring an expiratory temperature of the breathable liquid pumped out of the mammal's lungs; and
adjusting a temperature of the cooling fluid in function of the measured expiratory temperature for adjusting the temperature of the breathable liquid pumped into the lungs.

16. The method of claim 8, comprising a step of adjusting the temperature of the cooling fluid consisting in maintaining a flow of the cooling fluid during a first pre-set period of time, or stopping said flow during a second pre-set period of time, when the cooling fluid thermally exchanges with the breathable liquid.

17. The method according to claim 8, wherein the breathable liquid comprises perflurocarbons, or PFC.

18. The method according to claim 8, wherein the mammal is a human.

19. The method of claim 8, wherein reduction in real-time of the expiratory flow of the breathable liquid is by 50% while pumping the breathable liquid out of the lungs during an extended expiratory period of time in order to maintain a targeted end-expiratory breathable liquid volume, or EEBLV, in the mammal's lungs.

\* \* \* \* \*